(12) United States Patent
Kobashi et al.

(10) Patent No.: US 10,689,408 B2
(45) Date of Patent: Jun. 23, 2020

(54) BISPHOSPHONIC ACID COMPOUND

(71) Applicant: FUJIYAKUHIN CO., LTD., Saitama-shi (JP)

(72) Inventors: Seiichi Kobashi, Saitama (JP); Yoshinobu Aoyagi, Saitama (JP); Hiroshige Kato, Saitama (JP); Ryuko Tokuyama, Saitama (JP); Naoki Ashizawa, Saitama (JP); Koichi Ishida, Saitama (JP); Koji Matsumoto, Saitama (JP)

(73) Assignee: FUJIYAKUHIN CO., LTD., Saitama-shi (JP)

( * ) Notice: Subject to any disclaimer, the term of this patent is extended or adjusted under 35 U.S.C. 154(b) by 0 days.

(21) Appl. No.: 16/073,285

(22) PCT Filed: Jan. 27, 2017

(86) PCT No.: PCT/JP2017/002855
§ 371 (c)(1),
(2) Date: Jul. 26, 2018

(87) PCT Pub. No.: WO2017/131127
PCT Pub. Date: Aug. 3, 2017

(65) Prior Publication Data
US 2019/0002482 A1    Jan. 3, 2019

(30) Foreign Application Priority Data
Jan. 29, 2016 (JP) .................. 2016-027405

(51) Int. Cl.
C07F 9/38 (2006.01)
A61K 31/663 (2006.01)
A61P 9/00 (2006.01)
A61K 45/06 (2006.01)

(52) U.S. Cl.
CPC ............ *C07F 9/386* (2013.01); *A61K 31/663* (2013.01); *A61K 45/06* (2013.01); *A61P 9/00* (2018.01); *C07F 9/38* (2013.01); *C07F 9/3839* (2013.01); *C07F 9/3852* (2013.01); *C07F 9/3856* (2013.01); *C07F 9/3865* (2013.01)

(58) Field of Classification Search
None
See application file for complete search history.

(56) References Cited

U.S. PATENT DOCUMENTS

| | | |
|---|---|---|
| 2003/0027211 A1 | 2/2003 | Price |
| 2006/0166937 A1 | 7/2006 | Prescott |
| 2007/0275931 A1 | 11/2007 | Oldfield et al. |
| 2008/0255070 A1 | 10/2008 | Oldfield et al. |

FOREIGN PATENT DOCUMENTS

| | | |
|---|---|---|
| DE | 298 267 A5 | 2/1992 |
| JP | 62-114994 A | 5/1987 |
| JP | 7-507315 A | 8/1995 |
| JP | 7-508278 A | 9/1995 |
| JP | 2003-519183 A | 6/2003 |
| JP | 2006-504749 A | 2/2006 |
| JP | 2009-630414 A | 8/2009 |
| RU | 2079504 | 5/1997 |
| RU | 20865556 | 8/1997 |
| WO | WO 93/24496 A1 | 12/1993 |
| WO | WO 94/00129 A1 | 1/1994 |
| WO | WO 01/49295 A1 | 7/2001 |
| WO | WO 2004/035060 A1 | 4/2004 |
| WO | WO 2007/109585 A2 | 9/2007 |

OTHER PUBLICATIONS

Stefanucci et al., Medicinal Chemistry, 2015, 11, 417-431.*
Ito et al. in Cancer Science 94(1), 3-8 (2003).*
STN Registry entry for CAS RN 1957181-19-9, Entered STN Jul. 21, 2016, Accessed Nov. 12, 2019.*
Zhang et al., J. Med. Chem., 2007, 50, pp. 6067-6079.*
International Search Report dated Apr. 11, 2017, in PCT/JP2017/002855 filed Jan. 27, 2017.
Lu, K-C. et al. "Vascular Calcification and Renal Bone Disorders", The Scientific World Journal, vol. 2014, Article ID 637065, 2014, 20 pages.
Karwowski, W. et al., "The mechanism of vascular calcification—a systematic review". Med Sci Monit., vol. 18, No. 1, PMID: 22207127; 2012, pp. RA1-RA11.
Rocha-Singh, K.J. et al., "Peripheral Arterial Calcification: Prevalence, Mechanism, Detection, and Clinical Implications", Catheterization and Cardiovascular Interventions, vol. 83, 2014, pp. E-212-E220.

(Continued)

*Primary Examiner* — Alicia L Otton
(74) *Attorney, Agent, or Firm* — Oblon, McClelland, Maier & Neustadt, L.L.P.

(57) ABSTRACT

It is intended to provide a novel bisphosphonic acid compound or a salt thereof which shows a remarkable inhibitory effect on ectopic calcification, and a pharmaceutical composition comprising the same. The present invention provides a bisphosphonic acid compound represented by the following formula (1) or a pharmaceutically acceptable salt thereof:

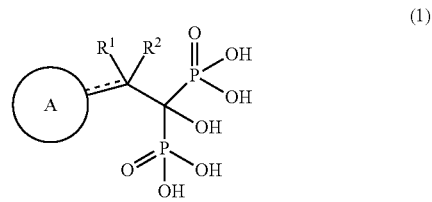

(1)

wherein ===== represents a single bond or a double bond; A represents a saturated cyclic hydrocarbon or a saturated heterocyclic ring comprising a sulfur atom or an oxygen atom; and $R^1$ and $R^2$ each independently represent an alkyl group, an alkenyl group, an alkynyl group, an alkoxy group, an aryloxy group, a haloalkoxy group, a haloalkyl group, a halogen atom or a hydrogen atom.

15 Claims, No Drawings

(56) References Cited

OTHER PUBLICATIONS

Guerin, A.P. et al., "Arterial stiffening and vascular calficifications in end-stage renal disease, Nephrology Dialysis Transplantation", vol. 15, 2000, pp. 1014-1021.
Giachelli, C.M. "Vascular Calcification Mechanisms", J. Am. Soc. Nephrol., vol. 15, 2004, 2959-2964.
Nitta, K. et al., "Effects of Cyclic Intermittent Etidronate Therapy on Coronary Artery Calcification in Patients Receiving Long-Term Hemodialysis", American Journal of Kidney Diseases, vol. 44, No. 4, 2004, pp. 680-688.
Koshiyama, H. et al., "Decrease in Carotid Intima-Media Thickness after 1-Year Therapy with Etidronate for Osteopenia Associated with Type 2 Diabetes", The Journal of Clinical Endocrinology & Metabolism, vol. 85, No. 8, 2000, pp. 2793-2796.
Toussaint, N.D. et al., "Effect of Alendronate on Vascular Calcification in CKD Stages 3 and 4. A Pilot Randomized Controlled Trial", American Journal of Kidney Diseases, vol. 56, No. 1, 2010, pp. 57-68.
Tanko, L.B. et al., "Effective doses of ibandronate do not influence the 3-year progression of aortic calcification in elderly osteoporotic women", Osteoporos Int, vol. 16. 2005, pp. 184-190.
Stefanucci, A. et al., "Investigation of the N-BP Binding at FPPS by Combined Computational Approaches" Medicinal Chemistry, vol. 11, 2015, pp. 417-431.
Drake, M.T. et al., "Bisphosphenates: Mechanism of Action and role in Clinical Practice", Mayo Clin Proc, vol. 83, No. 9, 2008, pp. 1032-1045.
Extended European Search Report dated Oct. 7, 2019, in Patent Application No. 17744357.9, citing documents AO and AX-AY therein, 8 pages.
Price, P. A. et al., "Bisphosphonates Alendronate and Ibandronate Inhibit Artery Calcification at Doses Comparable to Those That Inhibit Bone Resorption", Arteriosclerosis, Thrombosis, and Vascular Biology, XP002268657, vol. 21, No. 5, Jan. 1, 2001, pp. 817-824.
Hashiba, H. et al., Inhibitory Effects of Etidronate on the Progression of Vascular Calcification in Hemodialysis Patients, Therapeutic Apheresis and Dialysis, XP055356782, Jun. 1, 2004, pp. 241-247.
English Translation of Office Action as received in corresponding Russian Patent Application No. 2018130994, dated Mar. 13, 2020.

\* cited by examiner

BISPHOSPHONIC ACID COMPOUND

FIELD OF THE INVENTION

The present invention relates to a novel bisphosphonic acid compound or a salt thereof which shows a remarkable inhibitory effect on ectopic calcification, and a pharmaceutical composition comprising the same.

BACKGROUND OF THE INVENTION

Artificial dialysis is practiced for patients with end-stage renal failure through chronic renal failure as a result of progression of chronic kidney disease (CKD). CKD results in abnormal bone or mineral metabolism and causes a cardiovascular disease at a high incidence. This cardiovascular disease is the main cause of death in CKD patients. In CKD patients, a reduced bone mass as well as ectopic calcification including vascular calcification is observed with high frequency. The ectopic calcification is reported to be a process which is controlled by both progression and suppression. The main mechanisms of the ectopic calcification are considered to contain an attenuated process of suppression of calcification, induction of bone or cartilage formation, cell death, abnormal calcium and phosphorus homeostasis, the presence of calcium phosphate, substrate decomposition, etc. (Non Patent Literature 1).

Among the ectopic calcification cases, a phenomenon in which insoluble calcium phosphate, etc., is deposited in arterial vessels etc. is called vascular calcification. The vascular calcification is classified as follows: medial calcification, called Monckeberg's type, found in aged people, diabetic patients and CKD patients, and arteriosclerotic calcification of artherosclerotic plaques in the intima (atheroma intimal calcification) (Non Patent Literature 2). Examples of the former include ectopic calcification disorders (including induction by active vitamin D preparations) significantly found, particularly, in long-term artificial dialysis patients. On the other hand, the course of progression of the latter is considered to involve the accumulation of excessive lipids and macrophages to arteriosclerotic plaques as in the conventional mechanism of arteriosclerosis (Non Patent Literature 3).

The process of formation of Monckeberg's medial calcification presumably has a mechanism of differentiation of vascular smooth muscle cells to osteoblasts. Risk factors for vascular calcification include age, the duration of dialysis, diabetes mellitus, hypertension, phosphorus concentrations in blood, calcium-phosphate products, and medication with calcium-comprising phosphate binders (which are used for the purpose of treating secondary hyperparathyroidism in CKD), etc. (Non Patent Literature 4).

For CKD, it has been suggested that vascular calcification as a complication increases morbidities and mortalities of cardiovascular diseases (Non Patent Literature 5). Particularly, the treatment of vascular calcification is essential for decreasing the number of deaths of CKD patients.

However, treatment methods effective for ectopic calcification diseases and vascular calcification disorders have not yet been adequately established under these circumstances. For example, the administration of phosphate binders (calcium-comprising phosphate binders, polymeric phosphate binders, lanthanum carbonate, etc.) or calcium analogs has been attempted, but does not exert adequate drug efficacy. There has been a growing need of methods for effectively inhibiting and preventing vascular calcification with increase in CKD patients or patients with diseases involving arteriosclerosis. The development of novel effective medicines has been desired.

Etidronate, which is one of the bisphosphonate compounds, is effective as a therapeutic agent for osteoporosis by promoting increase in bone mass through its bone resorption inhibitory effect, while this compound shows the effect of inhibiting bone formation (bone calcification) at a higher dose than that produces the bone resorption inhibitory effect and is used as a therapeutic agent for ectopic ossification. In a test to which dialysis patients are subjected, etidronate has been reported to significantly inhibit calcification in the aorta (Non Patent Literature 6). Etidronate has further been reported to significantly decrease the carotid artery intima-media thicknesses of type 2 diabetic patients (Non Patent Literature 7).

According to the reports as to bisphosphonate compounds other than etidronate, nitrogen-comprising bisphosphonate drugs exhibited no calcification inhibitory effect in humans (Non Patent Literatures 8 and 9). There is also a report on the administration of bisphosphonate drugs to humans with the aim of ameliorating hypercalcemia, for example (Patent Literature 1). Furthermore, rat calcification models (Patent Literature 2), atherosclerosis models (Patent Literature 3) and rat hypercalcemia models (Patent Literature 4) have been reported as study cases of the effects of bisphosphonate compounds in animals. Although such reports, albeit a few in number, have been made, there is almost no finding about a bisphosphonate compound specific for ectopic calcification.

PATENT LITERATURE

[Patent Literature 1] JP-A-07-507315
[Patent Literature 2] JP-A-2003-519183
[Patent Literature 3] JP-A-2006-504749
[Patent Literature 4] JP-A-62-114994

Non Patent Literature

[Non Patent Literature 1] Lu K C, et al., Vascular calcification and renal bone disorders. Scientific World Journal. 2014; 2014: Article ID 637065
[Non Patent Literature 2] Karwowaki W, at al., The mechanism of vascular calcification—a systematic review. Mead Sci Monit. 2012; 18 (1): RA1-11
[Non Patent Literature 3] Rocha-Singh K J, et al., Peripheral arterial calcification: prevalence, mechanism, detection, and clinical implications. Catheter Cardiovasc Interv. 2014; 83 (6): E212-20
[Non Patent Literature 4] Guérin A P, et al., Arterial stiffening and vascular calcifications in end-stage renal disease. Nephrol Dial Transplant. 2000; 15 (7): 1014-21
[Non Patent Literature 5] Giachelli C M. Vascular calcification mechanisms. J Am Soc Nephrol. 2004; 15 (12): 2959-64
[Non Patent Literature 6] Nitta K, at al., Effects of cyclic intermittent etidronate therapy on coronary artery calcification in patients receiving long-term hemodialysis. Am J Kidney Dis. 2004; 44 (4): 680-8
[Non Patent Literature 7] Koshiyama H, et al., Decrease in carotid intima-media thickness after 1-year therapy with etidronate for osteopenia associated with type 2 diabetes. J Clin Endocrinol-Metab. 2000; 85 (8): 2793-6
[Non Patent Literature 8] Toussaint N D, et al., Effect of alendronate on vascular calcification in CKD stages 3 and 4: a pilot randomized controlled trial. Am J Kidney Dis. 2010; 56 (1): 57-68

[Non Patent Literature 9] Tankó L B, et al., Effective doses of ibandronate do not influence the 3-year progression of aortic calcification in elderly osteoporotic women. Osteoporos Int. 2005; 16 (2): 184-90

SUMMARY OF THE INVENTION

Problems to be Solved by the Invention

A calcification inhibitory effect or a bone resorption inhibitory effect influences the bone. The exertion of the former effect inhibits bone or cartilage calcification and tends to induce osteomalacia with bone density loss or a rise in inorganic phosphorus level in blood, whereas bisphosphonate drugs having a strong bone resorption inhibitory effect cause osteonecrosis of the jaw as an adverse reaction. In this respect, for treatment aimed at inhibiting ectopic calcification, there has been a demand for a highly safe bisphosphonate drug which secures a strong calcification inhibitory effect while its bone resorption inhibitory effect is not too strong, i.e., effects on the bone are not imbalanced, in order to circumvent the adverse reaction based on the bone resorption inhibitory effect.

An object of the present invention is to provide a novel bisphosphonic acid compound or a salt thereof which shows a remarkable ectopic calcification inhibitory effect, and a pharmaceutical composition comprising the same.

Means for Solving the Problems

The present inventors have conducted diligent studies to solve the problems, and consequently completed the present invention based on the finding that novel bisphosphonic acid compounds have a remarkable ectopic calcification inhibitory effect in rat calcification models through oral administration.

Specifically, the present invention provides the following [1] to [6]:

[1] A bisphosphonic acid compound represented by the following formula (1) or a pharmaceutically acceptable salt thereof:

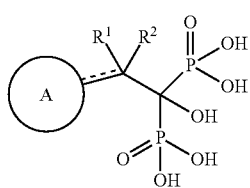

(1)

wherein ===== represents a single bond or a double bond; A represents a $C_{3-8}$ saturated cyclic hydrocarbon or a $C_{3-8}$ saturated heterocyclic ring comprising a sulfur atom or an oxygen atom (the saturated cyclic hydrocarbon or the saturated heterocyclic ring is optionally substituted by 1 to 6 groups selected from the group consisting of a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group and a halogen atom); and $R^1$ and $R^2$ each independently represent a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group, a halogen atom or a hydrogen atom, provided that when ===== is a double bond, R is absent.

[2] A pharmaceutical composition comprising a compound according to [1] or a salt thereof.

[3] A prophylactic or therapeutic drug for a disease associated with ectopic calcification, comprising a compound according to [1] or a salt thereof as an active ingredient.

[4] Use of a compound according to [1] or a salt thereof for the production of a prophylactic or therapeutic drug for a disease associated with ectopic calcification.

[5] The compound according to [1] or a salt thereof for preventing or treating a disease associated with ectopic calcification.

[6] A method for preventing or treating a disease associated with ectopic calcification, comprising administering an effective amount of a compound according to [1] or a salt thereof.

Effects of the Invention

The novel bisphosphonic acid compound of the present invention or a salt thereof is highly safe and shows an excellent ectopic calcification inhibitory effect. Thus, the novel bisphosphonic acid compound of the present invention or a salt thereof is useful in the prevention and treatment of a disease associated with ectopic calcification.

DETAILED DESCRIPTION OF THE INVENTION

Hereinafter, the present invention will be specifically described.

In the present specification, the "saturated cyclic hydrocarbon" may be any of monocyclic and polycyclic hydrocarbons. Examples of the $C_3$-$C_8$ cyclic hydrocarbon include a cyclopropane ring, a cyclobutane ring, a cyclopentane ring, a cyclohexane ring, a cycloheptane ring, a cyclooctane ring and a norbornane ring.

In the present specification, the "saturated heterocyclic ring" may be any of monocyclic and polycyclic heterocyclic rings. Examples of the $C_3$-$C_8$ saturated heterocyclic ring comprising a sulfur atom or an oxygen atom include a trimethylene oxide ring, a trimethylene sulfide ring, a tetrahydrofuran ring, a tetrahydrothiophene ring, a tetrahydropyran ring and a tetrahydrothiopyran ring.

In the present specification, the "alkyl group" means a saturated hydrocarbon chain which may be in any of linear, branched and cyclic forms, or a combination thereof. Examples of the $C_{1-6}$ alkyl group include a methyl group, an ethyl group, a n-propyl group, an isopropyl group, a n-butyl group, an isobutyl group, a s-butyl group, a t-butyl group, a n-pentyl group, a n-hexyl group, a cyclopropyl group, a cyclobutyl group and a cyclohexyl group.

In the present specification, the "alkenyl group" means an unsaturated hydrocarbon chain having a double bond which may be in any of linear, branched and cyclic forms, or a combination thereof. Examples of the $C_{2-6}$ alkenyl group include a vinyl group, a propenyl group and a butenyl group.

In the present specification, the "alkynyl group" means an unsaturated hydrocarbon chain having a triple bond which may be in any of linear and branched forms, or a combination thereof. Examples of the $C_{2-6}$ alkynyl group include an ethynyl group and a propynyl group.

In the present specification, examples of the "$C_{1-6}$ alkoxy group" include a methoxy group, an ethoxy group, a n-propoxy group, an isopropoxy group, a n-butoxy group, an isobutoxy group, a t-butoxy group, a n-pentoxy group, a n-hexyloxy group and a cyclopropoxy group. Examples of the "$C_{6-10}$ aryloxy group" include a phenoxy group and a naphthyloxy group.

In the present specification, examples of the "$C_{1-6}$ haloalkoxy group" include a trifluoromethoxy group and a trifluoroethoxy group.

In the present specification, examples of the "$C_{1-6}$ haloalkyl group" include a trifluoromethyl group and a trifluoroethyl group.

In the present specification, the "halogen atom" includes fluorine, chlorine, bromine and iodine.

In the formula (1), ===== represents a single bond or a double bond and is more preferably a single bond.

The $C_{3-8}$ saturated cyclic hydrocarbon represented by A is preferably cyclopropane, cyclobutane, cyclopentane, cyclohexane, cycloheptane, cyclooctane or norbornane. The $C_{3-8}$ saturated heterocyclic ring having a sulfur atom or an oxygen atom is preferably trimethylene oxide, trimethylene sulfide, tetrahydrofuran, tetrahydrothiophene, tetrahydropyran or tetrahydrothiopyran, more preferably tetrahydrofuran, tetrahydrothiophene, tetrahydropyran or tetrahydrothiopyran.

Substituents which can be added on the saturated cyclic hydrocarbon or the saturated heterocyclic ring are 1 to 6 groups selected from the group consisting of a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group and a halogen atom. Among them, 1 to 4 groups selected from the group consisting of a $C_{1-6}$ alkyl group, a $C_{1-6}$ alkoxy group, a $C_{6-10}$ aryloxy group and a halogen atom are preferred, and 1 or 2 groups selected from the group consisting of a $C_{1-6}$ alkyl group, a $C_{6-10}$ aryloxy group and a halogen atom are more preferred. The substitution positions of these substituents may be the bonding positions between the saturated cyclic hydrocarbon or the saturated heterocyclic ring and the single bond or the double bond.

$R^1$ and $R^2$ each represent a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group, a halogen atom or a hydrogen atom. Among them, a $C_{1-6}$ alkyl group, a halogen atom or a hydrogen atom is more preferred, and a $C_{1-3}$ alkyl group, a halogen atom or a hydrogen atom is further preferred.

In a more preferred embodiment, the compound of the formula (1) is a bisphosphonic acid compound or a pharmaceutically acceptable salt thereof wherein ===== represents a single bond; A represents a $C_{3-8}$ saturated cyclic hydrocarbon or a $C_{3-8}$ saturated heterocyclic ring comprising a sulfur atom or an oxygen atom (the saturated cyclic hydrocarbon or the saturated heterocyclic ring is optionally substituted by 1 to 4 groups selected from the group consisting of a $C_{1-6}$ alkyl group, a $C_{1-6}$ alkoxy group, a $C_{6-10}$ aryloxy group and a halogen atom); and $R^1$ and $R^2$ each independently represent a $C_{1-6}$ alkyl group, a halogen atom or a hydrogen atom.

In a further preferred embodiment, the compound of the formula (1) is a bisphosphonic acid compound or a pharmaceutically acceptable salt thereof wherein ===== represents a single bond; A represents a $C_{3-8}$ cyclic hydrocarbon or a $C_{3-8}$ saturated heterocyclic ring comprising a sulfur atom or an oxygen atom (the saturated cyclic hydrocarbon or the saturated heterocyclic ring is optionally substituted by 1 or 2 groups selected from the group consisting of a $C_{1-6}$ alkyl group, a $C_{6-10}$ aryloxy group and a halogen atom); and $R^1$ and $R^2$ each independently represent a $C_{1-3}$ alkyl group, a halogen atom or a hydrogen atom. Also, compounds described later in Examples or pharmaceutically acceptable salts thereof are further preferred.

The salt of the novel bisphosphonic acid compound of the present invention is a pharmaceutically acceptable salt of the compound of the formula (1) and can be produced by treating the compound of the formula (1) with a desired base in a solvent. Examples of the form of such a salt include a lithium salt, a potassium salt and a sodium salt. Sodium salt is preferred. The compound of the present invention also includes compounds labeled with various radioactive or nonradioactive isotopes.

The compound of the present invention represented by the formula (1) may exist as an isomer. For example, geometric isomers, optical isomers or diastereomers may be present. The present invention encompasses all of these isomers isolated, arbitrary mixtures thereof, racemates, etc.

A prodrug of the compound of the present invention represented by the formula (1) or a pharmaceutically acceptable salt thereof is also included as an equivalent compound thereof in the scope of claims of the present invention. The "prodrug" refers to a compound which is converted to the compound of the formula (1) under an in vivo metabolic mechanism, i.e., a compound which is converted to the compound of the formula (1) by, for example, enzymatic oxidation, reduction or hydrolysis or by hydrolysis, for example, gastric juice, in vivo. Examples of the prodrug of the compound of the formula (1) include compounds with a phosphoric group or a hydroxy group modified with, for example, an acyl group, an alkyl group or the like, for example, acetylated, pivaloylated or pivaloyloxymethylated compounds. These compounds can be synthesized from the compound of the formula (1) by methods known in the art. Alternatively, these prodrugs may be converted to the compound of the formula (1) under conditions as described in, for example, "The Organic chemistry of drug design and drug action (second edition)", chapter 8, p. 497-557.

The method for producing the compound of the present invention is not particularly limited, and the compound of the present invention can be produced according to, for example, steps given below. Also, the compounds labeled with various radioactive or nonradioactive isotopes, encompassed by the present invention, can be produced from isotope-substituted starting materials likewise as the production method described below.

Hereinafter, a typical method for producing the bisphosphonic acid compound of the present invention will be described.

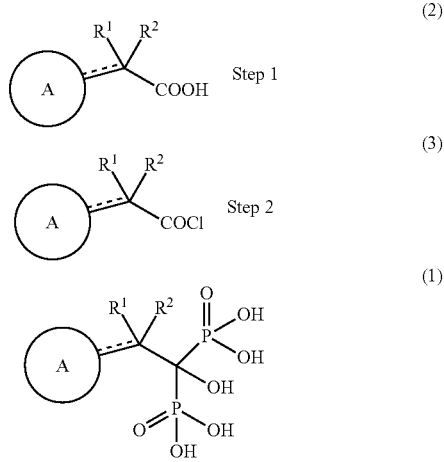

wherein $R^1$, $R^2$ and A are as defined above.

Step 1: A carboxylic acid intermediate (2) serving as a starting material can be reacted with, for example, thionyl chloride, phosphorus pentachloride, phosphorus trichloride, phosphorus oxychloride, oxalyl chloride in an organic solvent to produce an acid chloride (3).

Step 2: The acid chloride (3) can be reacted with, for example, tris(trimethylsilyl)phosphite in an organic solvent to produce a bisphosphonic acid compound (1). Alternatively, the acid chloride (3) can be reacted with phosphorus trichloride and phosphonic acid in an organic solvent to produce the bisphosphonic acid compound (1).

The carboxylic acid intermediate (2) for use in step 1 can be produced through reactions as shown below.

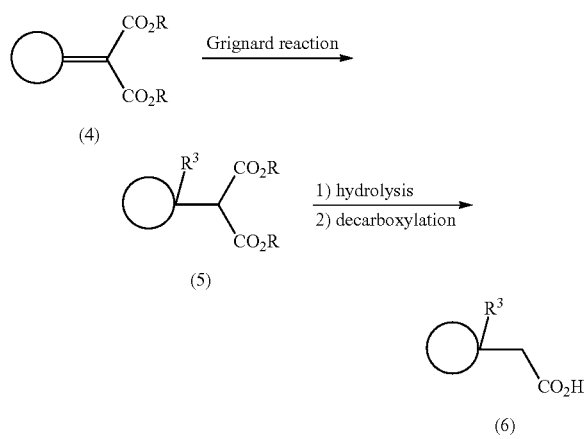

wherein R represents an ester residue, $R^3$ represents a substituent on the ring A, and A is as defined above.

(Method for Producing Carboxylic Acid Derivative (6) Substituted at Position 1 of Ring A)

For example, an alkyl group-, alkenyl group-, or alkynyl group-substituted carboxylic acid derivative (6) can be produced by converting a 2-cycloalkylidene malonic acid ester (4) to a malonic acid ester derivative (5) by alkylation, alkenylation or alkynylation and hydrolyzing the malonic acid ester derivative (5), followed by decarboxylation reaction. As for conditions for the alkylation, the alkenylation or the alkynylation, the compound of interest can be produced, for example, by Grignard reaction described in Shirley, D. A. Org. React., 1954, 8, 28. As for conditions for the decarboxylation, the compound of interest can be produced, for example, by adding an appropriate amount of an acid, if desired, without a solvent or in an organic solvent and heating the mixture.

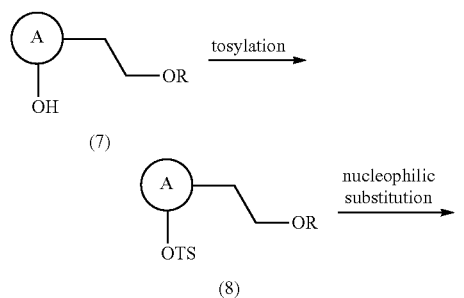

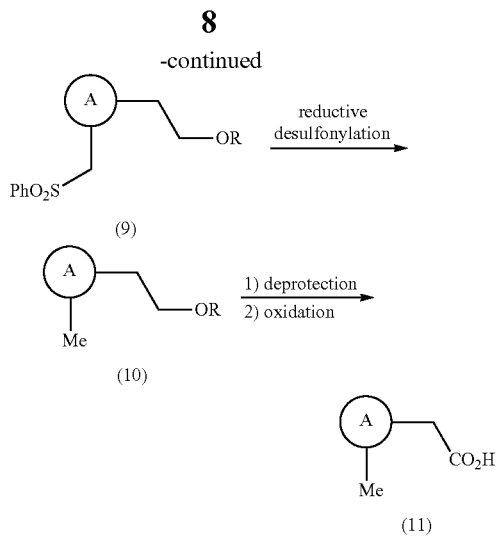

wherein R represents an alkyl group, and A is as defined above.

(Method for Synthesizing Methyl Group-Substituted Carboxylic Acid Derivative (11))

A carboxylic acid derivative (11) can be produced by tosylating a compound (7), then converting the obtained compound (8) to a compound (9) by sulfonylmethylation, and subsequently reductively desulfonylating the compound (9) into a compound (10), followed by deprotection and oxidation. Examples of conditions for the tosylation include a reaction with a tosylating agent such as tosyl chloride or tosylic anhydride in the presence of a base such as triethylamine, diisopropylethylamine or pyridine by the addition of a catalyst such as trimethylamine hydrochloride or N-methylimidazole in an organic solvent. Examples of conditions for the sulfonylmethylation include a reaction with a sulfone derivative having a sulfonylmethyl group, such as phenyl methyl sulfone, in the presence of a base such as n-butyllithium, s-butyllithium or t-butyllithium in an organic solvent such as tetrahydrofuran (hereinafter, referred to as THF) or diethyl ether. Examples of conditions for the reduction include use of a metal reducing agent such as magnesium in an alcohol solvent such as methanol or ethanol. In the case of using a protective group based on a silyl group, a deprotecting agent such as a hydrogen fluoride-pyridine complex or tetrabutylammonium fluoride can be used. Examples of conditions for the oxidation reaction include a method which involves obtaining an aldehyde by, for example, Dess-Martin oxidation, Swern oxidation, PCC oxidation, PDC oxidation, TEMPO oxidation and then converting the aldehyde to a carboxylic acid by Pinnick oxidation, and a method which involves reacting an oxidizing agent such as sodium chlorite with a catalytic amount of AZADO in an organic solvent supplemented with a weak acid such as citric acid or tartaric acid, water or a mixed solvent thereof to obtain a carboxylic acid.

-continued

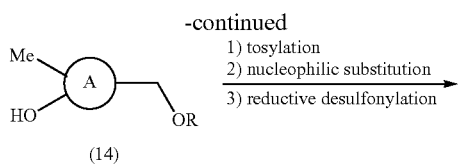

(14)

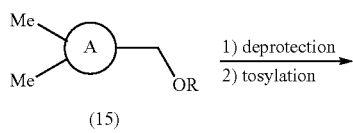

(15)

compound (18). Examples of conditions for the methylation include a reaction with a methylating agent such as methyllithium or methyl magnesium bromide by the addition of a catalyst in the presence of a Lewis acid. Examples of conditions for the reduction include conditions under which reduction is performed with a hydride reducing agent such as lithium aluminum hydride or lithium borohydride in an organic solvent such as THF or diethyl ether. Examples of the cyanation include a reaction with a cyanating agent such as sodium cyanide or potassium cyanide in an organic solvent, water, or a mixed solvent of water with an organic solvent.

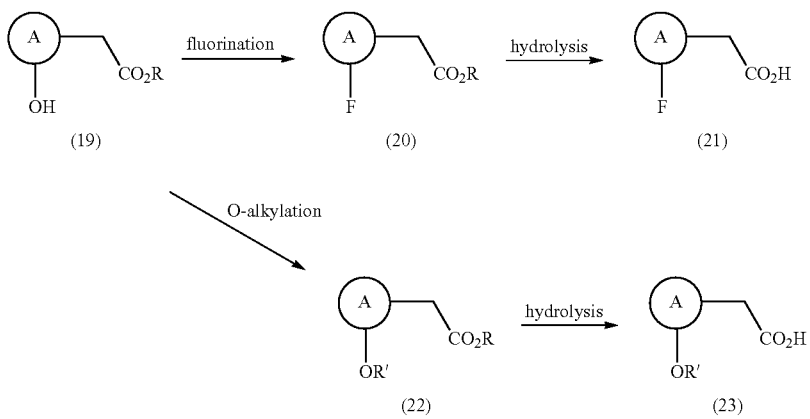

-continued

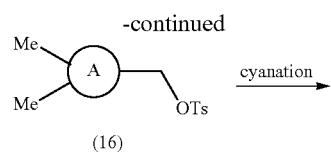

(16)

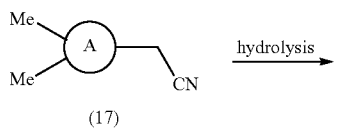

(17)

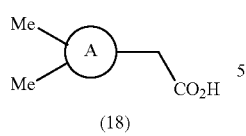

(18)

wherein R represents an alkyl group, and A is as defined above.

(Synthesis of Carboxylic Acid Derivative (18) Having Substituents on Adjacent Carbon Atoms)

For example, methyl 6-oxabicyclo[3.1.0]hexane-3-carboxylate (12) is methylated into a compound (13), which is then reduced and protected at its primary hydroxy group to obtain a compound (14). This compound (14) can be treated likewise as described the "Method for synthesizing methyl group-substituted carboxylic acid derivative (11)" to produce a compound (15). Subsequently, a compound (16) is obtained by deprotection and tosylation and cyanated into a compound (17), which can then be hydrolyzed to produce a wherein R represents an ester residue, R' represents an alkyl group or an aryl group, and A is as defined above.

(Method for Producing Fluorine Atom- or Alkoxy Group-Substituted Carboxylic Acid Derivative)

For example, a compound (19) is fluorinated into a compound (20), which can subsequently be hydrolyzed to obtain a compound (21). Examples of conditions for the fluorination include a reaction using a deoxy-fluorinating agent such as DAST or Deoxo-Fluor™ in an organic solvent. Alternatively, the compound (19) is converted by Mitsunobu reaction to a compound (22), which can then be hydrolyzed to obtain a compound (23). Examples of conditions for the Mitsunobu reaction include a method described in Hughes, D. L. Org. React., 1992, 42, 335.

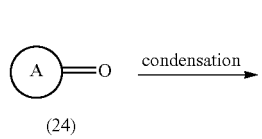

(24)

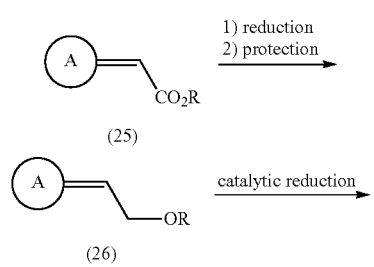

(25)

(26)

-continued

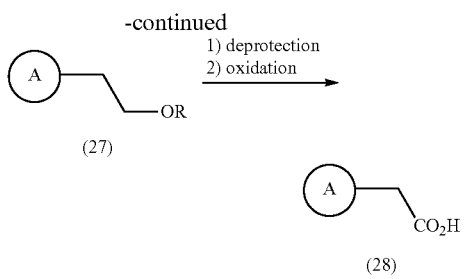

wherein R represents an alkyl group, and A is as defined above.

(Production Method Using Cyclic Ketone as Starting Material)

A cyclic ketone (24) is converted by Wittig reaction or Horner-Wadsworth-Emmons reaction to a compound (25), which is subsequently ester-reduced and then protected at its hydroxy group to obtain a compound (26). Subsequently, the compound (26) can be catalytically reduced into a compound (27), followed by deprotection and oxidation to obtain a compound (28). Examples of conditions for the Wittig reaction include conditions described in Maercker, A. Org. React., 1965, 14, 270. Examples of conditions for the Horner-Wadsworth-Emmons reaction include conditions described in Wadsworth, W. S., Jr. Org. React., 1977, 25, 73.

When a starting material or an intermediate for use in the method for producing the compound of the present invention has a functional group, the production can also be achieved by protection or deprotection using an appropriate protective group. Examples of such a functional group include an amino group, a hydroxy group and a carboxy group. Examples of the type of the protective group and the protection and deprotection methods include methods, etc., described in "Protective Groups in Organic Synthesis (Fourth Edition)" (Greene and Wuts).

When the method for producing the compound of the present invention requires hydrolysis reaction, the compound of interest can be produced by reaction at room temperature or under heating to reflux in the presence of an acid or a base in an amount appropriate for the reaction in an appropriate organic solvent, water, or a mixed solvent thereof. Examples of the acid include hydrochloric acid and sulfuric acid. Examples of the base include sodium hydroxide and lithium hydroxide.

The compound of the formula (1) thus synthesized can be isolated and purified as a free form or as a salt thereof by an ordinary chemical operation such as extraction, concentration, distillation, crystallization, filtration, recrystallization or various chromatography techniques. Also, optical isomers, stereoisomers or positional isomers, if present, can each be isolated by, for example, a fractional crystallization method, a chiral column method, a diastereomer method.

The compound of the present invention or the salt thereof exhibits an excellent ectopic calcification inhibitory effect as shown later in Examples. The ectopic calcification inhibitory effect is stronger than that of etidronate which is used as a therapeutic agent for ectopic ossification. Also, the ectopic calcification inhibitory effect of the compound of the present invention is stronger than its bone resorption inhibitory effect. Therefore, the compound of the present invention is excellent as an ectopic calcification inhibitor and is particularly useful as a prophylactic or therapeutic drug for a disease associated with ectopic calcification.

Examples of the disease associated with ectopic calcification include the following diseases: vascular calcification in dialysis and non-dialysis patients, calciphylaxis, diabetic angiopathy, soft tissue calcification, ectopic ossification (including ectopic ossification after hip arthroplasty, spinal damage, head trauma, etc.), rheumatism, osteoarthritis, fibrodysplasia ossificans progressiva, cancer, metastatic cancer, hypercalcemia, pachyderma, dermatomyositis, calcific tendinitis, bursitis calcarea, calcinosis circumscripta, calcinosis universalis, ossification of posterior longitudinal ligament of the cervical spine, ossification of spine ligament, hyperparathyroidism, abnormal vitamin D metabolism, vitamin D intoxication, arteriosclerosis, atherosclerosis, arteriolosclerosis, hypertensive arteriolosclerosis, Monckeberg's arteriosclerosis, heart valve stenosis, clot formation, uremia, diabetes mellitus, hypertension, Werner syndrome, pseudoxanthoma elasticum, angina pectoris, myocardial infarction, myocardial damage, heart failure, cardiac conduction disorder, cerebral infarction, metastatic calcification, dental calculus formation, periodontitis, bone or joint pain, bone deformation, fracture, myalgia, wound, inflammation, ischemic skin ulcer, urolithiasis, renal calculus, renal failure and chronic renal failure. The compound of the present invention is particularly effective for, for example, vascular calcification, calciphylaxis, arteriosclerosis, atherosclerosis, Monckeberg's arteriosclerosis in dialysis and non-dialysis patients.

In the present specification, the "vascular calcification" means the generation, growth or deposition of crystals of extracellular matrix hydroxyapatite (calcium phosphate) in vascular vessels. The vascular calcification includes calcification of the aorta, the coronary artery, the cusp and other vascular vessels. This calcification also includes medial calcification (Monckeberg's type) and calcification of artherosclerotic plaques in the intima (atheroma type).

The compound represented by the formula (1) or a pharmaceutically acceptable salt thereof may be used as it is or may be used as a pharmaceutical composition comprising one or two or more pharmaceutically acceptable carriers, for example, pharmaceutical additives. The pharmaceutical composition may be used in any dosage form and can be utilized as a tablet, a pill, a capsule, a powder, fine granules, granules, a solution, a suspension, a syrup, an injection, a formulation for external use, a suppository or the like.

The types of the pharmaceutical additives for use in the pharmaceutical composition comprising the compound represented by the formula (1) or a pharmaceutically acceptable salt thereof as an active ingredient are not particularly limited. For example, bases, excipients, lubricants, coating agents, sugar coating agents, wetting agents, binders, disintegrants, solvents, solubilizers, dissolving agents, dissolution aids, suspending agents, dispersing agents, emulsifiers, surfactants, tonicity agents, buffers, pH adjusters, soothing agents, antiseptics, preservatives, stabilizers, antioxidants, colorants and sweeteners described in the Japanese Pharmaceutical Excipients Dictionary (2007, Yakuji Nippo Ltd.) can each be used alone or in appropriate combination.

The compound of the present invention can be used in combination with an additional therapeutic or prophylactic agent for the disease for which the compound of the present invention may exhibit efficacy. The combined use means concurrent administration, or continuous administration or administration at desired intervals of time of individual drugs. A preparation for the concurrent administration may be a combination drug or a kit formulation.

For oral administration, one dose of the compound of the present invention or the salt thereof is usually approximately 0.01 to 100 mg/kg of body weight, which is administered once a day or once to three times a week. For intravenous administration, appropriate one dose thereof is approxi-

EXAMPLES

Hereinafter, the present invention will be specifically described with reference to Examples. However, the present invention is not intended to be limited by Examples below.

Abbreviations in Examples are as defined below.

$^{1}$H-NMR: proton nuclear magnetic resonance spectrum, $^{31}$P-NMR: phosphorus nuclear magnetic resonance spectrum, CDCl$_3$: deuterated chloroform, DMSO-d$_6$: deuterated dimethyl sulfoxide, D$_2$O: heavy water, Hz: hertz, J: coupling constant, m: multiplet, sept: septet, quint: quintet, q: quartet, dt: double triplet, dd: double doublet, ddd: double double doublet, t: triplet, d: doublet, s: singlet, br: broad, M: molar concentration, and N: normal. MS represents mass spectrometry. An instrument for ESI (electrospray ionization) as an ionization method was used. The compound of each Example was dissolved in 0.1% formic acid-acetonitrile and converted to a free form using Dowex 50×8 (H-Form) for measurement.

Example 1: Disodium (2-cyclopropyl-1-hydroxypropane-1,1-diyl)bisphosphonate

2-Cyclopropyipropionic acid (0.43 g) was dissolved in methylene chloride (4.0 mL). To the solution, thionyl chloride (0.35 mL) was added, and the mixture was stirred at 60° C. for 3 hours. The reaction solution was concentrated under reduced pressure. Tris(trimethylsilyl)phosphite (3.1 mL) was added to the residue under ice cooling, and the mixture was stirred at room temperature for 48 hours. Methanol (5.0 mL) was added to the reaction solution, and the mixture was stirred at room temperature for 1 hour. Then, the solvent was distilled off under reduced pressure. The obtained residue was dissolved in methanol (4.0 mL). To the solution, a 5 M solution of sodium methoxide in methanol (1.5 mL) was added at room temperature, and the mixture was stirred for 2 hours. Then, the reaction solution was filtered to obtain the title compound (1.10 g) as a colorless solid.

Example 2: Disodium (2-cyclobutyl-1-hydroxyethane-1,1-diyl)bisphosphonate

The title compound (0.70 g) was obtained as a colorless solid by synthesis likewise as described in Example 1 from cyclobutylacetic acid (0.34 g).

Example 3: Disodium (2-cyclobutyl-1-hydroxypropane-1,1-diyl)bisphosphonate

The title compound (0.75 g) was obtained as a colorless solid by synthesis likewise as described in Example 1 from 2-cyclobutyipropionic acid (0.45 g).

Example 4: Disodium [1-hydroxy-2-(1-methylcyclobutyl)ethane-1,1-diyl]bisphosphonate The title compound (0.65 g) was obtained as a colorless solid by synthesis likewise as described in Example 1 from (1-methylcyclobutyl)acetic acid (0.60 g).

Example 5: Disodium (2-cyclobutylidene-1-hydroxypropane-1,1-diyl)bisphosphonate

The title compound (0.92 g) was obtained as a colorless solid by synthesis likewise as described in Example 1 from 2-cyclobutylidenepropionic acid (0.50 g).

Example 6: Disodium (2-cyclopentyl-1-hydroxyethane-1,1-diyl)bisphosphonate

The title compound (0.74 g) was obtained as a colorless solid by synthesis likewise as described in Example 1 from cyclopentylacetic acid (0.31 g).

Example 7: Disodium (2-cyclopentylidene-1-hydroxyethane-1,1-diyl)bisphosphonate

The title compound (0.65 g) was obtained as a colorless solid by synthesis likewise as described in Example 1 from cyclopentylideneacetic acid (0.59 g).

Example 8: Disodium (2-cyclopentyl-1-hydroxypropane-1,1-diyl)bisphosphonate

The title compound (1.46 g) was obtained as a light brown solid by synthesis likewise as described in Example 1 from 2-cyclopentyipropionic acid (1.07 g).

Example 9: Disodium [1-hydroxy-2-(3-methylcyclopentyl)propane-1,1-diyl]bisphosphonate The title compound (0.50 g) was obtained as a colorless solid by synthesis likewise as described in Example 1 from 2-(3-methylcyclopentyl)propionic acid (0.47 g).

Example 10: Disodium (2-cyclopentylidene-1-hydroxypropane-1,1-diyl)bisphosphonate The title compound (0.51 g) was obtained as a colorless solid by synthesis likewise as described in Example 1 from 2-cyclopentylidenepropionic acid (0.23 g).

Example 11: Disodium [1-hydroxy-2-(1-methylcyclopentyl)ethane-1,1-diyl]bisphosphonate The title compound (3.20 g) was obtained as a colorless solid by synthesis likewise as described in Example 1 from (1-methylcyclopentyl)acetic acid (1.85 g).

Example 12: Disodium [2-(1-ethylcyclopentyl)-1-hydroxyethane-1,1-diyl]bisphosphonate The title compound (0.43 g) was obtained as a colorless solid by synthesis likewise as described in Example 1 from (1-ethylcyclopentyl)acetic acid (0.31 g).

Production Example 1

(a) Dimethyl 2-(1-propylcyclopentyl) malonate

To diethyl ether (8.5 mL), copper chloride (17 mg) and a 1 M solution of n-propyl magnesium bromide in THF (15 mL) were added at 0° C., and the mixture was stirred at room temperature for 1 hour. Then, a solution of dimethyl 2-cyclopentylidenemalonate (0.99 g) in diethyl ether (10 mL) was added dropwise thereto at 0° C., and the mixture was further stirred at room temperature for 2 hours. The reaction mately 0.0001 to 1 mg/kg of body weight, which is administered once a day or once to several times a month. The dose is appropriately determined according to each individual case in consideration of symptoms, age, sex, etc.

was terminated by the addition of 1 M hydrochloric acid (10 mL). The reaction solution was washed with brine and dried over anhydrous sodium sulfate. The solvent was distilled off under reduced pressure, and the obtained residue was purified by silica gel column chromatography to obtain a colorless oil (0.42 g).

$^1$H-NMR (CDCl$_3$, 270 MHz) δ: 0.88 (3H, t, J=7.2 Hz), 1.11-1.36 (2H, m), 1.40-1.51 (1H, m), 1.59-1.73 (7H, m), 1.75-1.97 (2H, m), 3.57 (1H, s), 3.71 (3H, s), 3.74 (3H, s).

(b) (1-Propylcyclopentyl)acetic acid

To a solution of dimethyl 2-(1-propylcyclopentyl)malonate (0.42 g) in methanol/THF (a 1:1) (4.0 mL), an 8 M NaOHaq (2.0 mL) was added at 0° C., and the mixture was stirred overnight at room temperature. The reaction was terminated by the addition of 6 M hydrochloric acid (4.0 mL) at 0° C., followed by extraction with ethyl acetate. The organic layer was washed with brine and dried over anhydrous sodium sulfate. The solvent was distilled off under reduced pressure, and the obtained residue was heated at 180° C. for 2 hours. Ethyl acetate was added to the residue, and the mixture was washed with water and brine. The reaction solution was dried over anhydrous sodium sulfate, and the solvent was distilled off under reduced pressure to obtain a brown oil (0.21 g).

$^1$H-NMR (CDCl$_3$, 270 MHz) δ: 0.90 (3H, t, J=6.9 Hz), 1.18-1.72 (12H, m), 2.33 (2H, s).

Example 13: Disodium [1-hydroxy-2-(1-propylcyclopentyl)ethane-1,1-diyl]bisphosphonate The title compound (0.36 g) was obtained as a colorless solid by synthesis likewise as described in Example 1 from (1-propylcyclopentyl)acetic acid (0.21 g) obtained in Production Example 1(b).

Example 14: Disodium [1-hydroxy-2-(2-methylcyclopentyl)ethane-1,1-diyl]bisphosphonate The title compound (0.64 g) was obtained as a colorless solid by synthesis likewise as described in Example 1 from (2-methylcyclopentyl)acetic acid (0.43 g).

Example 15: Disodium [1-hydroxy-2-(3-methylcyclopentyl)ethane-1,1-diyl]bisphosphonate The title compound (4.10 g) was obtained as a colorless solid by synthesis likewise as described: in Example 1 from (3-methylcyclopentyl)acetic acid (5.00 g).

Production Example 2

(a) (1R*,3S*)-3-(2-t-Butyldimethylailyloxyethyl) cyclopentyl acetate

To a solution of (1R*,3R*)-3-(2-t-butyldimethylsilyloxyethyl)cyclopentan-1-ol (2.33 g) in THF; (25 mL), triphenylphosphine (7.48 g), acetic acid (1.64 mL) and, diisopropyl azodicarboxylate (5.6 mL) were added, and the mixture was stirred at room temperature for 1 hour. The solvent was distilled off under reduced pressure. Ethylacetate (10 mL) and hexane (50 mL) were added to the residue, and insoluble matter was removed: The solvent was distilled off under reduced pressure. The obtained residue was used in the synthesis of (b).

(b) (1R*,3S*)-3-(2-t-Butyldimethylsilyloxyethyl) cyclopentan-1-ol

To a solution of (1R*,3S*)-3-(2-t-butyldimethylsilyloxyethyl)cyclopentyl acetate in methanol (10 mL), a 5 M solution of sodium methoxide in methanol (2.5 mL) was added, and the mixture was stirred at room temperature for 2 hours. The solvent was distilled off under reduced pressure, and water was added to the residue, followed by extraction with ethyl acetate. The organic layer was washed with brine and dried; over anhydrous sodium sulfate. The solvent was distilled off under reduced pressure; and the obtained residue was purified by silica gel column chromatography to obtain a colorless oil (2.05 g).

$^1$N-NMR (CDCl$_3$, 270 MHz) δ: 0.05 (6H, s), 0.89 (9H, s), 1.09-1.42 (3H, m), 1.47-1.61 (3H, m), 1.74-1.84 (1H, m), 1.88-2.05 (2H, m), 2.12-2.27 (1H, m), 3.62 (2H, t, J=6.9 Hz), 4.35 (1H, br).

(c) (1R*,3S*)-3-(2-t-Butyldimethylsilyloxyethyl) cyclopentyl 4-methylbenzenesulfonate To a solution of (1R*,3S*)-3-(2-t-butyldimethylsilyloxyethyl)cyclopentan-1-ol (2.05 g) in THP (40 mL), pyridine (1.0 mL), N-methylimidazole (1.0 mL) and tosyl chloride (3.19 g) were added, and the mixture was stirred at room temperature for 24 hours. Water was added thereto, and the mixture was stirred at room temperature for 2 hours. Then, the solvent was distilled off under reduced pressure, and 1 M hydrochloric acid was added to the residue, followed by extraction with ethyl acetate. The organic layer was washed with 1 M NaOHaq and brine and dried over anhydrous sodium sulfate. The solvent was distilled off under reduced pressure. The obtained residue was used in the synthesis of (d).

(d) t-Butyldimethyl {2-[(1R*,3S*)-3-(phenylsulfonylmethyl)cyclopentyl]ethoxy}silane To a solution of methyl phenyl sulfone (3.03 g) in THF (45 mL), a 2.65 M solution of n-butyllithium in n-hexane (7.2 mL) was added dropwise at 0° C., and the mixture was stirred at the same temperature as above for 5 minutes. A solution of (1R*,3S*)-3-(2-t-butyldimethylsilyloxyethyl)cyclopentyl 4-methylbenzenesulfonate in THF (15 mL) was added dropwise thereto, and the mixture was stirred at 55° C. for 3 hours. The reaction was terminated with a saturated aqueous solution of ammonium chloride, and the solvent was distilled off under reduced pressure. The obtained residue was diluted with ethyl acetate, washed with water and brine and dried over anhydrous sodium sulfate. The solvent was distilled off under reduced pressure, and the obtained residue was purified by silica gel column chromatography to obtain a colorless oil (1.86 g).

$^1$H-NMR (CDCl$_3$, 270 MHz) δ: 0.03 (6H, s), 0.88 (9H, s), 1.15-1.39 (2H, m), 1.46-1.60 (3H, m), 1.68-1.98 (3H, m), 2.03-2.14 (1H, m), 2.23-2.37 (1H, m), 3.14 (2H, d, J=6.8 Hz), 3.57 (2H, t, J=6.8 Hz), 7.53-7.69 (3H, m), 7.89-7.95 (2H, m).

(e) t-Butyldimethyl{2-[(1R*,3S*)-3-methylcyclopentyl]ethoxy}silane

To magnesium (1.77 g), THF (5.0 mL) and 0.98 M methyl magnesium bromide in THF (5 drops) were added, and the mixture was stirred at room temperature for 35 minutes. A solution of t-butyldimethyl{2-[(1R*,3S*)-3-(phenylsulfonylmethyl)cyclopentyl]ethoxy}silane (1.86 g) in methanol (40 mL) was added thereto, and the mixture was stirred at 50° C. for 3 hours. The reaction was terminated with a solution of 1 M hydrochloric acid-ethyl acetate (1:1), and the aqueous layer was subjected to extraction with ethyl acetate. The organic layer was washed with 1 M hydrochloric acid and brine and dried over anhydrous sodium sulfate. The solvent was distilled off under reduced pressure, and the obtained residue was purified by silica gel column chromatography to obtain a colorless oil (0.75 g).

$^1$H-NMR (CDCl$_3$, 270 MHz) δ: 0.05 (6H, s), 0.62-0.72 (1H, m), 0.96 (9H, s), 0.97 (3H, d, J=6.5 Hz), 1.09-1.30 (2H, m), 1.49-1.60 (2H, m), 1.67-1.78 (2H, m), 1.83-1.97 (3H, m), 3.60 (2H, t, J=6.5 Hz).

(f) 2-[(1R*,3S*)-3-Methylcyclopentyl]ethanol

To a solution of t-butyldimethyl{2-[(1R*,3S*)-3-methylcyclopentyl]ethoxy}silane (0.64 g) in THF (6 mL), a 1 M solution of tetrabutylammonium fluoride in THF (4.0 mL) was added, and the mixture was stirred at room temperature for 1 hour. The solvent was distilled off under reduced pressure, and the obtained residue was purified by silica gel column chromatography to obtain a colorless oil (0.21 g).

$^1$H-NMR (CDCl$_3$, 270 MHz) δ: 0.61-0.77 (1H, m), 0.98 (3H, d, J=6.2 Hz), 1.08-1.34 (3H, m), 1.52-1.64 (1H, m), 1.67-1.81 (2H, m), 1.83-1.99 (3H, m), 3.65 (2H, t, J=6.8 Hz).

(g) (1R*,3S*)-(3-Methylcyclopentyl)acetic acid

To a solution of 2-[(1R*,3S*)-3-methylcyclopentyl]ethanol (0.46 g) in acetonitrile (5.0 mL), water (5.0 mL), citric acid (1.04 g), sodium chlorite (0.61 g) and 2-azaadamantane-N-oxyl (55 mg) were added, and the mixture was stirred at room temperature for 1 hour. The reaction was terminated with sodium hydrogen sulfite, and the solvent was distilled off under reduced pressure. The obtained residue was dissolved in 1 M NaOHaq. The solution was washed with diisopropyl ether, and 4 M hydrochloric acid was added thereto, followed by extraction with ethyl acetate. The organic layer was washed with brine and dried over anhydrous sodium sulfate, and the solvent was distilled off under reduced pressure to obtain a colorless oil (0.32 g).

$^1$H-NMR (CDCl$_3$, 270 MHz) δ: 0.67-0.83 (1H, m), 0.99 (3H, d, J=6.5 Hz), 1.10-1.39 (2H, m), 1.67-2.12 (4H, m), 2.17-2.41 (3H, m).

Example 16: Disodium {1-hydroxy-2-[(1R*,3S*)-3-methylcyclopentyl]ethane-1,1-diyl}bisphosphonate The title compound (0.52 g) was obtained as a colorless solid by synthesis likewise as described in Example 1 from (1R*,3S*)-(3-methylcyclopentyl)acetic acid (0.32 g) obtained in Production Example 2(g).

Example 17: Disodium {1-hydroxy-2-[(1R*,3R*)-3-methylcyclopentyl]ethane-1,1-diyl}bisphosphonate The title compound (0.98 g) was obtained as a colorless solid by synthesis likewise as described in Example 1 from (1R*,3R*)-(3-methylcyclopentyl)acetic acid (0.46 g).

Production Example 3

(a) Methyl (1R*,3S*)-(3-fluorocyclopentyl)acetate

To a solution of methyl (1R*,3S*)-(3-hydroxycyclopentyl)acetate (0.59 g) in dichloromethane (5.0 mL), Deoxo-Fluor™ (0.81 mL) was added at 0° C., and the mixture was stirred at room temperature for 20 hours. The reaction was terminated by the addition of a saturated aqueous solution of sodium bicarbonate (5.0 mL), and the organic layer was washed with brine and dried over anhydrous sodium sulfate. The solvent was distilled off under reduced pressure. The obtained residue was used in the synthesis of (b).

(b) (1R*, 3S*)-(3-Fluorocyclopentyl) acetic acid

To methyl (1R*,3S*)-(3-fluorocyclopentyl)acetate, methanol (7.4 mL) and 2 N NaOHaq (3.7 mL) were added, and the mixture was stirred at room temperature for 5 hours. The solvent was distilled off under reduced pressure, and 1 N hydrochloric acid was added to the residue, followed by extraction with ethyl acetate. The organic layer was dried over anhydrous sodium sulfate. The solvent was distilled off under reduced pressure, and the obtained residue was purified by silica gel column chromatography to obtain a colorless solid (0.18 g).

$^1$H-NMR (CDCl$_3$, 270 MHz) δ: 1.23-1.50 (2H, m), 1.60-2.09 (4H, m), 2.23-2.43 (3H, m), 5.02-5.26 (1H, m), 12.03 (1H, br).

Example 18: Disodium {2-[(1R*,3R*)-3-fluorocyclopentyl]-1-hydroxyethane-1,1-diyl}bisphosphonate The title compound (0.24 g) was obtained as a colorless solid by synthesis likewise as described in Example 1 from (1R*,3S*)-(3-fluorocyclopentyl)acetic acid (0.18 g) obtained in Production Example 3(b).

Production Example 4

The following compounds were synthesized likewise as described in Production Example 3.

(a) Methyl (1R*,3R*)-(3-fluorocyclopentyl)acetate $^1$H-NMR (CDCl$_3$, 270 MHz) δ: 1.42-2.46 (9H, m), 3.67 (3H, s), 5.00-5.24 (1H, m).

(b) (1R*,3R*)-(3-Fluorocyclopentyl) acetic acid $^1$H-NMR (CDCl$_3$, 270 MHz) δ: 1.18-2.31 (9H, m), 4.98-5.26 (1H, m).

Example 19: Disodium {2-[(1R*,3S*)-3-fluorocyclopentyl]-1-hydroxyethane-1,1-diyl}bisphosphonate The title compound (0.34 g) was obtained as a colorless solid by synthesis likewise as described in Example 1 from (1R*,3R*)-(3-fluorocyclopentyl)acetic acid (0.22 g) obtained in Production Example 4(b).

Production Example 5

(a) Methyl (1R*,3R*)-(3-phenoxycyclopentyl)acetate

To a solution of methyl (1R*,3S*)-(3-hydroxycyclopentyl)acetate (1.44 g) in THF (20 mL), a solution of phenol (1.03 g) in THF (10 mL) and triphenylphosphine (3.59 g) were added, then diisopropyl azodicarboxylate (2.7 mL) was added dropwise at 0° C., and the mixture was stirred at room temperature for 30 minutes. The reaction solution was diluted with ethyl acetate, washed with a saturated aqueous solution of sodium bicarbonate and brine and dried over anhydrous sodium sulfate. The solvent was distilled off under reduced pressure, and the obtained residue was purified by silica gel column chromatography to obtain a colorless oil (0.64 g).

$^1$H-NMR (CDCl$_3$, 270 MHz) δ: 1.20-1.35 (1H, m), 1.47-1.58 (1H, m), 1.83-1.92 (1H, m), 2.00-2.19 (3H, m), 2.37 (2H, d, J=7.3 Hz), 2.54-2.66 (1H, m), 3.67 (3H, s), 4.76-4.80 (1H, m), 6.85 (2H, d, J=7.6 Hz), 6.91 (1H, t, J=7.3 Hz), 7.26 (2H, t, J=8.0 Hz).

(b) (1R*,3R*)-(3-Phenoxycyclopentyl)acetic acid

To methyl (1R*,3R*)-(3-phenoxycyclopentyl)acetate (0.64 g), methanol (14 mL) and 2 N NaOHaq (6.8 mL) were added, and the mixture was stirred at room temperature for 18 hours. The solvent was distilled off under reduced pressure, and 1 N hydrochloric acid was added to the residue, followed by extraction with ethyl acetate. The organic layer was dried over anhydrous sodium sulfate. The solvent was distilled off under reduced pressure to obtain a colorless oil (0.60 g).

$^1$H-NMR (CDCl$_3$, 270 MHz) δ: 1.13-1.30 (1H, m), 1.44-1.74 (2H, m), 1.84-2.46 (6H, m), 4.78-4.86 (1H, m), 6.84-6.93 (3H, m), 7.26 (2H, t, J=8.1 Hz), 11.99 (1H, br).

Example 20: Disodium {1-hydroxy-2-[(1R*,3R*)-3-phenoxycyclopentyl]ethane-1,1-diyl}bisphosphonate The title compound (0.94 g) was obtained as a colorless solid by synthesis likewise as described in Example 1 from (1R*,3R)-(3-phenoxycyclopentyl)acetic acid obtained in Production Example 5(b).

Example 21: Disodium [2-(3,3-dimethylcyclopentyl)-1-hydroxyethane-1,1-diyl]bisphosphonate The title compound (0.30 g) was obtained as a colorless solid by synthesis likewise as described in Example 1 from (3,3-dimethylcyclopentyl)acetic acid (0.37 g).

Example 22: Disodium [2-(3,3-dimethylcyclopentylidene)-1-hydroxyethane-1,1-diyl]bisphosphonate The title compound (0.48 g) was obtained as a colorless solid by synthesis likewise as described in Example 1 from (3,3-dimethylcyclopentylidene) acetic acid (0.47 g).

Example 23: Disodium [2-(3,3-difluorocyclopentyl)-1-hydroxyethane-1,1-diyl]bisphosphonate The title compound (0.06 g) was obtained as a colorless solid by synthesis likewise as described in Example 1 from (3,3-difluorocyclopentyl)acetic acid (0.11 g).

Production Example 6

(a) Methyl (1R*,3S*,4S*)-3-hydroxy-4-methylcyclopentane-1-carboxylate

To a solution of copper cyanide (1.82 g) in THF (25 mL), a 3.1 M solution of methyllithium in diethoxymethane (13 mL) was added dropwise at −78° C., and the mixture was stirred at the same temperature as above for 10 minutes, at 0° C. for 15 minutes and at −78° C. for 10 minutes. A solution of methyl (1R,3s,5S)-6-oxabicyclo[3.1.0]hexane-3-carboxylate (1.31 g) in THF (15 mL) and a boron trifluoride-diethyl ether complex (4.6 mL) were added dropwise thereto at −78° C., and the mixture was stirred for 20 minutes. The reaction was terminated by the addition of a saturated aqueous solution of ammonium chloride (15 mL), and insoluble matter was removed by celite filtration. The filtrate was subjected to extraction with ethyl acetate, and the organic layer was dried over anhydrous sodium sulfate. The solvent was distilled off under reduced pressure, and the obtained residue was purified by silica gel column chromatography to obtain a colorless oil (1.29 g).

$^1$H-NMR (CDCl$_3$, 270 MHz) δ: 1.05 (3H, d, J=7.0 Hz), 1.37-1.51 (1H, m), 1.78-1.92 (2H, m), 2.18-2.28 (2H, m), 3.00 (1H, quint, J=8.9 Hz), 3.68 (3H, m), 3.81-3.92 (1H, m).

(b) (1R*,2R*,4S*)-4-(Hydroxymethyl)-2-methylcyclopentan-1-ol

To a solution of methyl (1R*,3S*,4S*)-3-hydroxy-4-methylcyclopentane-1-carboxylate (0.30 g) obtained in Production Example 6(a) in THF (10 mL), lithium-aluminum hydride (0.14 g) was added at 0° C., and the mixture was stirred at room temperature for 30 minutes. The reaction was terminated by the addition of 10% NaOHaq, and insoluble matter was removed by celite filtration. Then, the organic layer was dried over anhydrous sodium sulfate. The solvent was distilled off under reduced pressure. The obtained residue was used in the synthesis of (c).

(c) (1R*,2R*,4S*)-2-Methyl-4-(triisopropylsilyloxymethyl)cyclopentan-1-ol

To a solution of (1R*,2R*,4S*)-4-(hydroxymethyl)-2-methylcyclopentan-1-ol obtained in Production Example 6(b) in dichloromethane (8.5 mL), imidazole (0.15 g) was added, then triisopropylsilyl chloride (0.40 mL) was added dropwise at 0° C., and the mixture was stirred at the same temperature as above for 5 hours. The solvent was distilled off under reduced pressure, and the obtained residue was purified by silica gel column chromatography to obtain a colorless oil (0.37 g).

$^1$H-NMR (CDCl$_3$, 270 MHz) δ: 1.01-1.10 (24H, m), 1.41-2.05 (5H, m), 2.26-2.34 (1H, m), 3.56 (2H, dd, J=5.9, 1.1 Hz), 3.67-3.79 (1H, m).

(d) (1R*,2R*,4S*)-2-Methyl-4-(triisopropylsilyloxymethyl)cyclopentyl 4-methylbenzenesulfonate To a solution of (1R*,2R*,4S*)-2-methyl-4-(triisopropylsilyloxymethyl)cyclopentan-1-ol (0.37 g) obtained in Production Example 6(c) in dichloromethane (5.0 mL), N,N-dimethyl-4-aminopyridine (39 mg) and pyridine (0.26 mL) were added, and p-toluenesulfonyl chloride (0.36 g) was added 0° C. The mixture was stirred at room temperature for 14 hours, and then, the solvent was distilled off under reduced pressure. The obtained residue was diluted with ethyl acetate, washed with 1 M hydrochloric acid, water, a saturated aqueous solution of sodium bicarbonate, water and brine and dried over anhydrous sodium sulfate. The solvent was distilled off under reduced pressure, and the obtained residue was purified by silica gel column chromatography to obtain a colorless oil (93 mg).

$^1$H-NMR (CDCl$_3$, 270 MHz) δ: 0.90 (3H, d, J=7.0 Hz), 0.97-1.07 (21H, m), 1.62-2.31 (6H, m), 2.44 (3H, s), 3.47-3.58 (2H, m), 4.39 (1H, q, J=5.9 Hz), 7.32 (2H, d, J=8.3 Hz), 7.79 (2H, d, J=8.3 Hz).

(e) Triisopropyl{(1R*,3S*,4R*)-[3-methyl-4-(phenylsulfonylmethyl)cyclopentyl]methoxy}silane To a solution of methyl phenyl sulfone (0.22 g) in THF (4.0 mL), 2.6 M n-butyllithium in n-hexane (0.52 mL) was added dropwise at 0° C., and the mixture was stirred at the same temperature as above for 5 minutes. A solution of (1R*,2R*,4S*)-2-methyl-4-(triisopropylsilyloxymethyl)cyclopentyl 4-methylbenzenesulfonate (0.20 g) obtained in Production Example 6(d) in THF (3.0 mL) was added dropwise thereto, and the mixture was stirred at 55° C. for 13 hours. The reaction was terminated with a saturated aqueous solution of ammonium chloride, and the solvent was distilled off under reduced pressure. The obtained residue was diluted with ethyl acetate, washed with water and brine and dried over anhydrous sodium sulfate. The solvent was distilled off under reduced pressure, and the obtained residue was purified by silica gel column chromatography to obtain a colorless oil (64 mg).

$^1$H-NMR (CDCl$_3$, 270 MHz) δ: 0.82 (3H, d, J=7.0 Hz), 0.98-1.30 (23H, m), 1.85-2.44 (5H, m), 3.05 (1H, dd, J=14.0, 8.4 Hz), 3.22 (1H, dd, J=14.0, 5.4 Hz), 3.57 (2H, d, J=5.9 Hz), 7.53-7.68 (3H, m), 7.90-7.94 (2H, m).

(f) (1r,3R,4S)-[(3,4-Dimethylcyclopentyl)methoxy]triisopropylsilane

To magnesium (0.11 g), THP (0.50 mL) and 2 M methyl magnesium chloride in THF (3 drops) were added, and the mixture was stirred at room temperature for 15 minutes. A solution of triisopropyl{(1R*,3S*,4R*)-[3-methyl-4-(phenylsulfonylmethyl)cyclopentyl]methoxy}silane (0.13 g) obtained in Production Example 6(e) in methanol (5.0 mL) was added thereto, and the mixture was stirred at 50° C. for 17 hours. The reaction was terminated with a solution of 1 M hydrochloric acid-ethyl acetate (1:1), and the aqueous layer was subjected to extraction with ethyl acetate. The organic layer was washed with a 1 M NaOHaq and brine and dried over anhydrous sodium sulfate. The solvent was distilled off under reduced pressure, and the obtained residue was purified by silica gel column chromatography to obtain a colorless oil (46 mg).

$^1$H-NMR (CDCl$_3$, 270 MHz) δ: 0.85 (6H, d, J=6.5 Hz), 0.99-1.12 (23H, m), 1.82-2.14 (5H, m), 3.58 (2H, d, J=6.5 Hz).

(g) (1r,3R,4S)-(3,4-Dimethylcyclopentyl)methanol

To a solution of (1r,3R,4S)-[(3,4-dimethylcyclopentyl)methoxy]triisopropylsilane (0.42 g) obtained in Production Example 6(f) in THF (5.0 mL), a 1 M solution of tetrabutylammonium fluoride in THF (1.8 mL) was added at 0° C., and the mixture was stirred at room temperature for 16 hours. The solvent was distilled off under reduced pressure, and the obtained residue was purified by silica gel column chromatography to obtain a colorless oil (0.21 g).

$^1$H-NMR (CDCl$_3$, 270 MHz) δ: 0.86 (6H, d, J=6.8 Hz), 0.92-1.05 (2H, m), 1.27 (1H, br), 1.85-2.19 (5H, m), 3.54 (2H, d, J=5.4 Hz).

(h) (1r,3R,4S)-(3,4-Dimethylcyclopentyl)methyl 4-methylbenzenesulfonate

To a solution of (1r,3R,4S)-(3,4-dimethylcyclopentyl)methanol (0.21 g) obtained in Production Example 6(g) in dichloromethane (5.0 mL), triethylamine (0.41 mL), N-methylimidazole (0.15 mL) and tosyl chloride (0.44 g) were added, and the mixture was stirred at room temperature for 7 hours. The solvent was distilled off under reduced pressure, and the obtained residue was diluted with ethyl acetate, washed with 1 M hydrochloric acid, water, a saturated aqueous solution of sodium bicarbonate, water and brine and dried over anhydrous sodium sulfate. The solvent was distilled off under reduced pressure. The obtained residue was used in the synthesis of (i).

(i) (1r,3R,4S)-(3,4-Dimethylcyclopentyl)acetonitrile

To a solution of (1r,3R,4S)-(3,4-dimethylcyclopentyl)methyl 4-methylbenzenesulfonate obtained in Production Example 6(h) in N,N-dimethylformamide (7.0 mL), sodium cyanide (0.15 g) was added, and the mixture was stirred at 75° C. for 7 hours. The reaction solution was diluted with water, followed by extraction with diethyl ether. The organic layer was washed with water and brine and dried over anhydrous sodium sulfate. The solvent was distilled off under reduced pressure. The obtained residue was used in the synthesis of (j).

(j) (1r,3R,4S)-(3,4-Dimethylcyclopentyl)acetic acid

To (1r,3R,4S)-(3,4-dimethylcyclopentyl) acetonitrile obtained in Production Example 6(i), methanol (3.7 mL) and 2 N NaOHaq (7.4 mL) were added, and the mixture was stirred at 100° C. for 20 hours. The solvent was distilled off under reduced pressure, and 1 N hydrochloric acid was added to the residue, followed by extraction with ethyl acetate. The organic layer was dried over anhydrous sodium sulfate. The solvent was distilled off under reduced pressure to obtain a colorless oil (0.18 g).

$^1$H-NMR (CDCl$_3$, 270 MHz) δ: 0.86 (6H, J=6.2 Hz), 0.91-0.99 (2H, m), 1.96-2.10 (4H, m), 2.15-2.32 (1H, m), 2.37 (2H, d, J=7.0 Hz).

Example 24: Disodium {2-[(1r,3R,4S)-3,4-dimethylcyclopentyl]-1-hydroxyethane-1,1-diyl}bisphosphonate The title compound (0.30 g) was obtained as a colorless solid by synthesis likewise as described in Example 1 from (1r,3R,4S)-(3,4-dimethylcyclopentyl)acetic acid (0.17 g) obtained in Production Example 6(j).

Production Example 7

The following compounds were synthesized likewise as described in Production Example 6.

(a) Methyl (1R*,3R*,4R*)-3-hydroxy-4-methylcyclopentane-1-carboxylate $^1$H-NMR (CDCl$_3$, 270 MHz) δ: 0.98 (3H, d, J=6.5 Hz), 1.84-2.29 (6H, m), 2.84-2.95 (1H, m), 3.72 (3H, s), 3.75-3.83 (1H, m).

(b) (1R*, 2R*,4R*)-2-Methyl-4-(triisopropylsilyloxymethyl)cyclopentan-1-ol $^1$H-NMR (CDCl$_3$, 270 MHz) δ: 0.91 (3H, d, J=7.0 Hz), 1.03-1.47 (23H, m), 1.81-1.97 (2H, m), 2.10-2.32 (2H, m), 2.63 (1H, d, J=7.6 Hz), 3.59-3.68 (3H, m).

(c) (1R*,2R*,4R*)-2-Methyl-4-(triisopropylsilyloxymethyl)cyclopentyl 4-methylbenzenesulfonate $^1$H-NMR (CDCl$_3$, 270 MHz) δ: 0.87 (3H, d, J=7.0 Hz), 1.00-1.09 (21H, m), 1.22-1.76 (3H, m), 1.97-2.17 (3H, m), 2.44 (3H, s), 3.51-3.57 (2H, m), 4.37 (1H, q, J=6.8 Hz), 7.32 (2H, d, J=8.1 Hz), 7.79 (2H, d, J=8.1 Hz).

(d) Triisopropyl{(1R*,3R*,4S*)-[3-methyl-4-(phenylsulfonylmethyl)cyclopentyl]methoxy}silane $^1$H-NMR (CDCl$_3$, 270 MHz) δ: 0.80 (3H, d, J=7.0 Hz), 0.98-1.08 (21H, m), 1.40-1.66 (4H, m), 2.19-2.40 (3H, m), 3.01 (1H, dd, J=14.1, 7.8 Hz), 3.19 (1H, dd, J=14.1, 5.7 Hz), 3.51 (2H, d, J=7.3 Hz), 7.53-7.68 (3H, m), 7.89-7.93 (2H, m).

(e) (1s,3R,4S)-[(3,4-Dimethylcyclopentyl)methoxy]triisopropylsilane $^1$H-NMR (CDCl$_3$, 270 MHz) δ: 0.83 (6H, d, J=6.5 Hz), 1.00-1.10 (21H, m), 1.33-1.51 (4H, m), 1.91-2.02 (2H, m), 2.21-2.33 (1H, m), 3.52 (2H, d, J=6.5 Hz).

(f) (1s,3R,4S)-(3,4-Dimethylcyclopentyl)methanol $^1$H-NMR (CDCl$_3$, 270 MHz) δ: 0.85 (6H, d, J=6.5 Hz), 1.41-1.62 (4H, a), 1.91-2.07 (2H, m), 2.29 (1H, sept, J=8.1 Hz), 3.48 (2H, d, J=7.3 Hz).

(g) (1s,3R,4S)-(3,4-Dimethylcyclopentyl)acetic acid $^1$H-NMR (CDCl$_3$, 270 MHz) δ: 0.84 (6H, d, J=6.8 Hz), 1.37-1.47 (2H, m), 1.58-1.66 (2H, m), 1.98-2.10 (2H, m), 2.34 (2H, d, J=7.8 Hz), 2.42-2.60 (1H, m).

Example 25: Disodium {2-[(1s,3R,4S)-3,4-dimethylcyclopentyl]-1-hydroxyethane-1,1-diyl}bisphosphonate The title compound (0.50 g) was obtained as a colorless solid by synthesis likewise as described in Example 1 from (1s,3R,4S)-(3,4-dimethylcyclopentyl)acetic acid (0.29 g).

Production Example 8

(a) Ethyl (3,3,4,4-tetramethylcyclopentylidene)acetate

To a solution of hexamethyldisilazane (0.75 g) in THF (5.0 mL), a 2.65 M solution of n-butyllithium in n-hexane (1.8 mL) and triethyl phosphonoacetate (0.86 mL) were added under ice cooling, and the mixture was stirred for 10 minutes. A solution of 3,3,4,4-tetramethylcyclopentanone (0.50 g) in THF (5.0 mL) was added thereto under ice cooling, and the mixture was stirred at room temperature for 5 hours. The solvent was distilled off under reduced pressure, and the obtained residue was diluted with ethyl acetate, washed with water and brine and dried over anhydrous sodium sulfate. The solvent was distilled off under reduced pressure, and the obtained residue was purified by silica gel column chromatography to obtain a colorless oil (0.54 g).
$^1$H-NMR (CDCl$_3$, 270 MHz) δ: 0.90 (6H, s), 0.92 (6H, s), 1.27 (3H, t, J=7.0 Hz), 2.42 (2H, s), 2.75 (2H, s), 4.14 (2H, q, J=7.0 Hz), 5.73 (1H, quint, J=2.7 Hz).

(b) 2-(3,3,4,4-Tetramethylcyclopentylidene)ethanol

To a solution of ethyl (3,3,4,4-tetramethylcyclopentylidene)acetate (0.52 g) obtained in Production Example 8(a) in THF (10 mL), a 1.04 M solution of diisobutyl aluminum in n-hexane (6.0 mL) was added, and the mixture was stirred at room temperature for 15 minutes. The reaction was terminated by the addition of 1 M hydrochloric acid, followed by extraction with ethyl acetate. The organic layer was washed with brine and dried over anhydrous sodium sulfate, and the solvent was distilled off under reduced pressure. The obtained residue was purified by silica gel column chromatography to obtain a colorless oil (0.42 g).
$^1$H-NMR (CDCl$_3$, 270 MHz) δ: 0.87 (6H, s), 0.90 (6H, s), 2.23 (2H, 8), 2.26 (2H, s), 4.09 (2H, br), 5.41-5.49 (1H, m).

(c) Triisopropyl[2-(3,3,4,4-tetramethylcyclopentylidene)ethoxy]silane

To a solution of 2-(3,3,4,4-tetramethylcyclopentylidene)ethanol (0.25 g) obtained in Production Example 8(b) in dichloromethane (5.0 mL), imidazole (0.20 g) and triisopropylsilyl chloride (0.38 mL) were added, and the mixture was stirred at room temperature for 15 minutes. The reaction was terminated by the addition of 1 M hydrochloric acid, followed by extraction with ethyl acetate. The organic layer was washed with brine and dried over anhydrous sodium sulfate, and the solvent was distilled off under reduced pressure. The obtained residue was purified by silica gel column chromatography to obtain a colorless oil (0.54 g).
$^1$H-NMR (CDCl$_3$, 270 MHz) δ: 0.86 (6H, s), 0.88 (6H, s), 1.02-1.10 (21H, m), 2.14 (2H, s), 2.25 (2H, S), 4.15-4.21 (2H, m), 5.34-5.42 (1H, m).

(d) Triisopropyl [2-(3,3,4,4-tetramethylcyclopentyl)ethoxy]silane

To a solution of triisopropyl[2-(3,3,4,4-tetramethylcyclopentylidene)ethoxy]silane (0.54 g) obtained in Production Example 8(c) in ethyl acetate (5.0 mL), St palladium-activated carbon (0.11 g) was added, and the mixture was stirred at room temperature for 18 hours in a hydrogen atmosphere. Insoluble matter was removed by celite filtration, and the solvent was distilled off under reduced pressure. The obtained residue was used in the synthesis of (e).
$^1$H-NMR (CDCl$_3$, 270 MHz) δ: 0.84 (6H, s), 0.85 (6H, s), 1.00-1.08 (21H, m), 1.28 (2H, dd, J=13.0, 7.3 Hz), 1.60 (2H, d, J=7.0 Hz), 1.73 (2H, dd, J=13.0, 9.7 Hz), 1.97-2.14 (1H, m), 3.63 (2H, t, J=7.0 Hz).

(e) 2-(3,3,4,4-Tetramethylcyclopentyl)ethanol

To a solution of triisopropyl[2-(3,3,4,4-tetramethylcyclopentyl)ethoxy]silane obtained in Production Example 8(d) in THF (5.0 mL), a 1 M solution of tetrabutylammonium fluoride in THF (2.2 mL) was added, and the mixture was stirred at room temperature for 1 hour. The solvent was distilled off under reduced pressure, and the obtained residue was purified by silica gel column chromatography to obtain a colorless oil (0.22 g).
$^1$H-NMR (CDCl$_3$, 270 MHz) δ: 0.85 (6H, s), 0.86 (6H, s), 1.29 (2H, dd, J=13.0, 7.3 Hz), 1.62 (2H, q, J=7.3 Hz), 1.75 (2H, dd, J=13.0, 9.5 Hz), 2.02-2.16 (1H, m), 3.62 (2H, t, J=6.8 Hz).

(f) (3,3,4,4-Tetramethylcyclopentyl)acetic acid

To a solution of 2-(3,3,4,4-tetramethylcyclopentyl) ethanol (0.22 g) obtained in Production Example 8(e) in acetonitrile (2.0 mL), water (2.0 mL), citric acid (0.37 g), sodium chlorite (0.22 g) and 2-azaadamantane-N-oxyl (10 mg) were added, and the mixture was stirred at room temperature for 1 hour. The reaction was terminated with sodium hydrogen sulfite, and the solvent was distilled off under reduced pressure. The obtained residue was dissolved in 1 M NaOHaq. The solution was washed with diisopropyl ether, and 4 M hydrochloric acid was added thereto, followed by extraction with ethyl acetate. The organic layer was washed with brine and dried over anhydrous sodium sulfate, and the solvent was distilled off under reduced pressure to obtain a colorless oil (0.22 g).

$^1$H-NMR (CDCl$_3$, 270 MHz) δ: 0.86 (6H, s), 0.87 (6H, s), 1.32 (2H, dd, J=13.2, 7.3 Hz), 1.84 (2H, dd, J=13.2, 9.2 Hz), 2.36-2.52 (3H, m).

Example 26: Disodium [1-hydroxy-2-(3,3,4,4-tetramethylcyclopentyl)ethane-1,1-diyl]bisphosphonate The title compound (0.36 g) was obtained as a colorless solid by synthesis likewise as described in Example 1 from (3,3,4,4-tetramethylcyclopentyl)acetic acid (0.22 g) obtained in Production Example 8(f).

Example 27: Disodium (2-cyclohexyl-1-hydroxyethane-1,1-diyl)bisphosphonate

The title compound (12.7 g) was obtained as a colorless solid by synthesis likewise as described in Example 1 from cyclohexylacetic acid (6.0 g).

Example 28: Disodium (2-cyclohexyl-1-hydroxypropane-1,1-diyl)bisphosphonate

The title compound (0.13 g) was obtained as a colorless solid by synthesis likewise as described in Example 1 from 2-cyclohexyipropionic acid (0.34 g).

Example 29: Disodium [2-(4,4-dimethylcyclohexyl)-1-hydroxypropane-1,1-diyl]bisphosphonate The title compound (1.15 g) was obtained as a colorless solid by synthesis likewise as described in Example 1 from 2-(4,4-dimethylcyclohexyl)propionic acid (0.80 g).

Example 30: Disodium [1-hydroxy-2-(1-methylcyclohexyl)ethane-1,1-diyl]bisphosphonate The title compound (0.51 g) was obtained as a colorless solid by synthesis likewise as described in Example 1 from (1-methylcyclohexyl) acetic acid (0.34 g).

Example 31: Disodium [2-(bicyclo[2.2.1]heptan-2-yl)-1-hydroxyethane-1,1-diyl]bisphosphonate The title compound (1.20 g) was obtained as a colorless solid by synthesis likewise as described in Example 1 from (bicyclo[2.2.1]heptan-2-yl)acetic acid (0.60 g).

Example 32: Disodium [2-(bicyclo[2.2.1]heptan-2-yl)-1-hydroxypropane-1,1-diyl]bisphosphonate The title compound (1.29 g) was obtained as a colorless solid by synthesis likewise as described in Example 1 from 2-(bicyclo[2.2.1]heptan-2-yl)propionic acid (0.76 g).

Example 33: Disodium [(1R*,2S*,4S*)-2-(bicyclo[2.2.1]heptan-2-yl)-1-hydroxyethane-1,1-diyl]bisphosphonate The title compound (1.84 g) was obtained as a colorless solid by synthesis likewise as described in Example 1 from (1R*,2S*,4S*)-(bicyclo[2.2.1]heptan-2-yl)acetic acid (1.12 g).

Example 34: Disodium [(1R*,2R*,4S*)-2-(bicyclo[2.2.1]heptan-2-yl)-1-hydroxyethane-1,1-diyl]bisphosphonate The title compound (1.46 g) was obtained as a colorless solid by synthesis likewise as described in Example 1 from (1R*,2R*,4S*)-(bicyclo[2.2.1]heptan-2-yl)acetic acid (1.00 g).

Example 35: Disodium [1-hydroxy-2-(3,3,5,5-tetramethylcyclohexyl)ethane-1,1-diyl]bisphosphonate The title compound (0.60 g) was obtained as a colorless solid by synthesis likewise as described in Example 1 from (3,3,5,5-tetramethylcyclohexyl)acetic acid (0.60 g).

Production Example 9

(a) Ethyl (3,3,5,5-tetramethylcyclohexylidene)acetate

A colorless oil (1.5 g) was obtained by synthesis likewise as described in Production Example 8(a) from 3,3,5,5-tetramethylcyclohexan-1-one (2.31 g).

$^1$H-NMR (CDCl$_3$, 270 MHz) δ: 0.96 (6H, s), 0.98 (6H, s), 1.28 (3H, t, J=7.1 Hz), 1.33 (2H, s), 1.96 (2H, s), 2.62 (2H, s), 4.15 (2H, q, J=7.1 Hz), 5.69 (1H, s).

(b) (3,3,5,5-Tetramethylcyclohexylidene)acetic acid

To ethyl (3,3,5,5-tetramethylcyclohexylidene)acetate obtained in Production Example 9(a), methanol (5.0 mL), THP (5.0 mL) and 4 M NaOHaq (10 mL) were added, and the mixture was stirred at room temperature for 5 hours. The solvent was distilled off under reduced pressure, and 1 M hydrochloric acid was added to the residue, followed by extraction with ethyl acetate. The organic layer was dried over anhydrous sodium sulfate. The solvent was distilled off under reduced pressure to obtain a colorless solid (1.94 g).

$^1$H-NMR (CDCl$_3$, 270 MHz) δ: 0.97 (6H, s), 0.99 (6H, s), 1.35 (2H, s), 1.96 (2H, s), 2.63 (2H, s), 5.73 (1H, s).

Example 36: Disodium [1-hydroxy-2-(3,3,5,5-tetramethylcyclohexylidene) ethane-1,1-diyl]bisphosphonate The title compound (0.74 g) was obtained as a colorless solid by synthesis likewise as described in Example 1 from (3,3,5,5-tetramethylcyclohexylidene)acetic acid (0.59 g) obtained in Production Example 9(b).

Example 37: Disodium [1-hydroxy-2-((1r,4r)-4-methylcyclohexyl]ethane-1,1-diyl)bisphosphonate The title compound (1.38 g) was obtained as a colorless solid by synthesis likewise as described in Example 1 from (1r,4r)-(4-methylcyclohexyl)acetic acid (1.00 g).

Example 38: Disodium [2-(4,4-dimethylcyclohexyl)-1-hydroxyethane-1,1-diyl]bisphosphonate The title compound (0.61 g) was obtained as a colorless solid by synthesis likewise as described in Example 1 from (4,4-dimethylcyclohexyl)acetic acid (0.39 g).

Example 39: Disodium [1-hydroxy-2-(4-propylcyclohexyl)ethane-1,1-diyl]bisphosphonate The title compound (1.98 g) was obtained as a colorless solid by synthesis likewise as described in Example 1 from (4-propylcyclohexyl)acetic acid (1.13 g).

Example 40: Disodium [1-hydroxy-2-(tetrahydro-2H-thiopyran-4-yl)ethane-1,1-diyl]bisphosphonate The title compound (0.35 g) was obtained as a colorless solid by synthesis likewise as described in Example 1 from (tetrahydrothiopyran-4-yl)acetic acid (0.19 g).

Example 41: Disodium ([1-hydroxy-2-(tetrahydrothiophen-3-yl)ethane-1,1-diyl]bisphosphonate The title compound (0.28 g) was obtained as a colorless solid by synthesis likewise as described in Example 1 from (tetrahydrothiophen-3-yl)acetic acid (0.14 g).

Example 42: Disodium [1-hydroxy-2-(tetrahydrothiophen-3-yl)propane-1,1-diyl]bisphosphonate The title compound (0.47 g) was obtained as a colorless solid by synthesis likewise as described in Example 1 from 2-(tetrahydrothiophen-3-yl)propionic acid (0.33 g).

Example 43: Disodium [1-hydroxy-2-(tetrahydro-2H-pyran-4-yl) ethane-1,1-diyl]bisphosphonate The title compound (1.12 g) was obtained as a colorless solid by synthesis likewise as described in Example 1 from (tetrahydro-2H-pyran-4-yl)acetic acid (1.16 g).

Example 44: Disodium (2-cycloheptyl-1-hydroxyethane-1,1-diyl)bisphosphonate

The title compound (1.20 g) was obtained as a colorless solid by synthesis likewise as described in Example 1 from cycloheptylacetic acid (0.69 g).

Example 45: Disodium (2-cycloheptyl-1-hydroxypropane-1,1-diyl)bisphosphonate The title compound (1.50 g) was obtained as a colorless solid by synthesis likewise as described in Example 1 from 2-cycloheptylpropionic acid (1.00 g).

Example 46: Disodium (2-cyclooctyl-1-hydroxyethane-1,1-diyl)bisphosphonate

The title compound (1.60 g) was obtained as a colorless solid by synthesis likewise as described in Example 1 from cyclooctylacetic acid (0.98 g).

Example 47: (2-Cyclohexyl-1-hydroxyethane-1,1-diyl)bisphosphonic acid

To the compound (20.0 g) of Example 27, water (300 mL) and Dowex 50×8 (H-Form) (159 mL) were added, and the mixture was stirred at room temperature for 19 hours. The reaction solution was filtered and then concentrated under reduced pressure to obtain the title compound (17.2 g) as a colorless solid.

Example 48: Dilithium (2-cyclohexyl-1-hydroxyethane-1,1-diyl)bisphosphonate

To the compound (0.58 g) of Example 47, water (9.0 mL), ethanol (9.0 mL) and lithium hydroxide monohydrate (0.17 g) were added, and the mixture was stirred for 2 hours. Then, the reaction solution was filtered to obtain the title compound (0.51 g) as a colorless solid.

Example 49: Tetrasodium (2-cyclohexyl-1-hydroxyethane-1,1-diyl)bisphosphonate To the compound (0.29 g) of Example 47, water (6.0 mL), methanol (6.0 mL) and a 5 M solution of sodium methoxide in methanol (0.80 mL) were added, and the mixture was stirred at room temperature for 2 hours. Then, the reaction solution was filtered to obtain the title compound (0.37 g) as a colorless solid.

Example 50: Dipotassium (2-cyclohexyl-1-hydroxyethane-1,1-diyl)bisphosphonate To the compound (0.30 g) of Example 47, water (5.0 mL) and potassium hydroxide (0.14 g) were added, and the mixture was stirred at room temperature for 18 hours. The reaction solution was concentrated under reduced pressure to obtain the title compound (0.37 g) as a colorless solid.

TABLE 1

| Ex. | structure | Data |
|---|---|---|
| Example 1 | 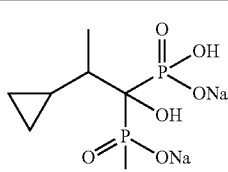 | $^1$H-NMR (D$_2$O, 270 MHz) δ: 0.01-0.23 (1H, m), 0.34-0.63 (3H, m), 1.00-1.20 (1H, m), 1.31 (3H, d, J = 7.3 Hz), 1.60-1.78 (1H, m). MS m/z: 259 (M − 2Na + H)$^+$. |

TABLE 1-continued

| Ex. | structure | Data |
|---|---|---|
| Example 2 | 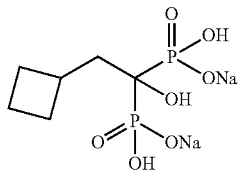 | $^1$H-NMR (D$_2$O, 270 MHz) δ: 1.65-1.95 (4H, m), 2.00-2.20 (4H, m), 2.70-2.92 (1H, m). MS m/z: 259 (M − 2Na + H)$^+$. |
| Example 3 | 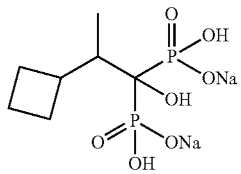 | $^1$H-NMR (D$_2$O, 270 MHz) δ: 1.09 (3H, d, J = 7.3 Hz), 1.57-2.22 (7H, m), 2.70-2.9 (1H, m). MS m/z: 273 (M − 2Na + H)$^+$. |
| Example 4 | 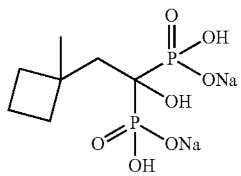 | $^1$H-NMR (D$_2$O, 270 MHz) δ: 1.36 (3H, s), 1.62-2.01 (4H, m), 2.06 (2H, t, J = 8.5 Hz), 2.19 (2H, t, J = 13.0 Hz). MS m/z: 273 (M − 2Na + H)$^+$. |
| Example 5 | 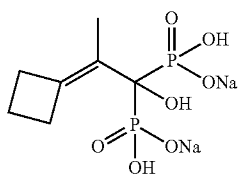 | $^1$H-NMR (D$_2$O, 270 MHz) δ: 1.72 (3H, s), 1.92 (2H, quint, J = 8.1 Hz), 2.63-2.78 (2H, m), 2.91-3.08 (2H, m). MS m/z: 271 (M − 2Na + H)$^+$. |
| Example 6 | 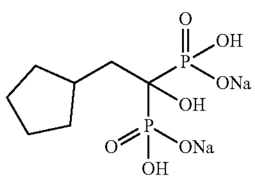 | $^1$H-NMR (D$_2$O, 270 MHz) δ: 1.11-1.27 (2H, m), 1.44-1.71 (4H, m), 1.87-2.00 (2H, m), 2.03-2.17 (2H, m), 2.18-2.31 (1H, m). MS m/z: 273 (M − 2Na + H)$^+$. |
| Example 7 | 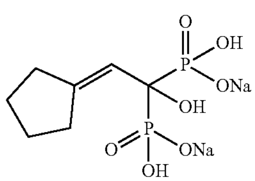 | $^1$H-NMR (D$_2$O, 270 MHz) δ: 1.43-1.82 (4H, m), 2.29-2.45 (2H, m), 2.49-2.62 (2H, m), 5.61 (1H, br). MS m/z: 271 (M − 2Na + H)$^+$. |
| Example 8 | 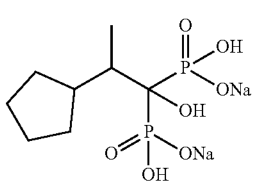 | $^1$H-NMR (D$_2$O, 270 MHz) δ: 1.12 (3H, d, J = 6.5 Hz), 1.18-1.35 (2H, m), 1.35-1.60 (4H, m), 1.73-1.89 (2H, m), 2.15-2.49 (2H, m). MS m/z: 287 (M − 2Na + H)$^+$. |

TABLE 2

| Ex. | structure | Data |
|---|---|---|
| Example 9 | 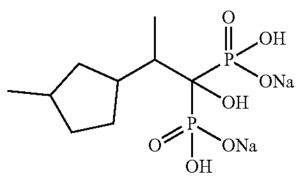 | ¹H-NMR (D₂O, 270 MHz) δ: 0.82-1.20 (8H, m), 1.20-1.50 (1H, m), 1.58-2.02 (4H, m), 2.18-2.40 (1H, m), 2.56-2.87 (1H, m).<br>MS m/z: 301 (M − 2Na + H)⁺. |
| Example 10 | 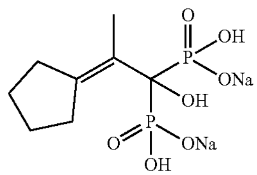 | ¹H-NMR (D₂O, 270 MHz) δ: 1.46-1.70 (4H, m), 1.86 (3H, s), 2.18-2.32 (2H, m), 2.50-2.68 (2H, m).<br>MS m/z: 285 (M − 2Na + H)⁺. |
| Example 11 | 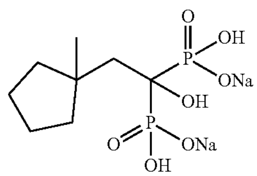 | ¹H-NMR (D₂O, 270 MHz) δ: 1.17 (3H, s), 1.45-1.72 (8H, m), 2.19 (2H, t, J = 14.4 Hz).<br>MS m/z: 287 (M − 2Na + H)⁺. |
| Example 12 | 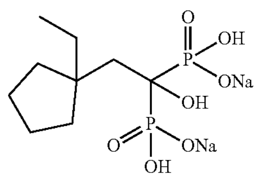 | ¹H-NMR (D₂O, 270 MHz) δ: 0.86 (3H, t, J = 7.6 Hz), 1.42-1.73 (10H, m), 2.15 (2H, t, J = 14.7 Hz).<br>MS m/z: 301 (M − 2Na + H)⁺. |
| Example 13 | 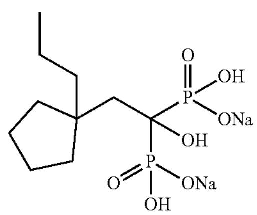 | ¹H-NMR (D₂O, 270 MHz) δ: 0.85 (3H, t, J = 7.0 Hz), 1.22-1.43 (2H, m), 1.44-1.73 (10H, m), 2.15 (2H, t, J = 14.7 Hz).<br>MS m/z: 315 (M − 2Na + H)⁺. |
| Example 14 | 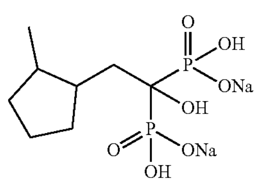 | ¹H-NMR (D₂O, 270 MHz) δ: 0.76-0.97 (3H, m), 1.01-1.93 (7H, m), 1.94-2.40 (3H, m).<br>MS m/z: 287 (M − 2Na + H)⁺. |
| Example 15 | 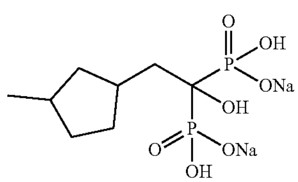 | ¹H-NMR (D₂O, 270 MHz) δ: 0.63-0.84 (1H, m), 0.85-0.99 (3H, m), 0.99-1.36 (2H, m), 1.40-1.52 (1H, m), 1.62-2.14 (5H, m), 2.19-2.49 (1H, m).<br>MS m/z: 287 (M − 2Na + H)⁺. |
| Example 16 | 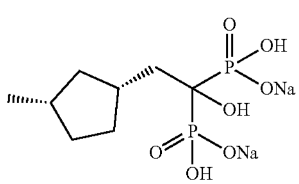 | ¹H-NMR (D₂O, 270 MHz) δ: 0.76 (1H, q, J = 10.8 Hz), 0.95 (3H, d, J = 6.8 Hz), 1.07-1.37 (2H, m), 1.64-1.79 (1H, m), 1.81-1.96 (2H, m), 1.98-2.15 (3H, m), 2.19-2.34 (1H, m).<br>MS m/z: 287 (M − 2Na + H)⁺. |

TABLE 3

| Ex. | structure | Data |
|---|---|---|
| Example 17 | 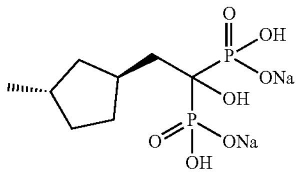 | ¹H-NMR (D₂O, 270 MHz) δ: 0.94 (3H, d, J = 6.8 Hz), 1.03-1.28 (2H, m), 1.43-1.54 (2H, m), 1.73-1.86 (1H, m), 1.90-2.11 (4H, m), 2.36-2.50 (1H, m).<br>MS m/z: 287 (M − 2Na + H)⁺. |
| Example 18 | 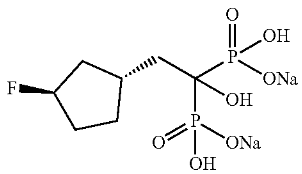 | ¹H-NMR (D₂O, 270 MHz) δ: 1.18-2.35 (8H, m), 2.47-2.68 (1H, m), 5.12-5.39 (1H, m).<br>MS m/z: 291 (M − 2Na + H)⁺. |
| Example 19 | 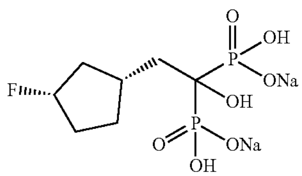 | ¹H-NMR (D₂O, 270 MHz) δ: 1.28-2.50 (9H, m), 5.08-5.36 (1H, m).<br>MS m/z: 291 (M − 2Na + H)⁺. |
| Example 20 | 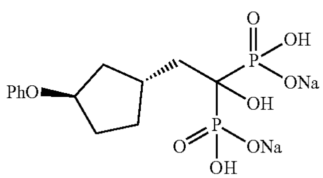 | ¹H-NMR (D₂O, 270 MHz) δ: 1.23-1.44 (1H, m), 1.54-1.81 (2H, m), 1.97-2.30 (5H, m), 2.49-2.70 (1H, m), 4.89-4.99 (1H, m), 6.89-7.09 (3H, m), 7.38 (2H, t, J = 8.1 Hz).<br>MS m/z: 365 (M − 2Na + H)⁺. |
| Example 21 | 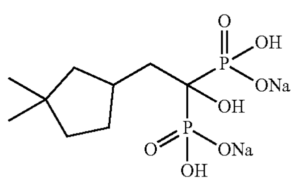 | ¹H-NMR (D₂O, 270 MHz) δ: 0.72-1.00 (1H, m), 0.83 (3H, s), 0.87 (3H, s), 1.10-1.34 (3H, m), 1.52-1.69 (1H, m), 1.76-1.99 (3H, m), 2.23-2.45 (1H, m).<br>MS m/z: 301 (M − 2Na + H)⁺. |
| Example 22 | 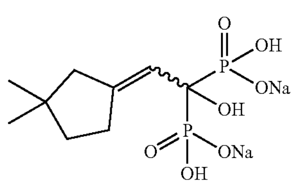 | ¹H-NMR (D₂O, 270 MHz) δ: 0.78-1.00 (6H, m), 1.20-1.60 (2H, m), 1.93-2.31 (2H, m), 2.32-2.74 (2H, m), 5.30-5.48 (1H, m).<br>MS m/z: 299 (M − 2Na + H)⁺. |
| Example 23 | 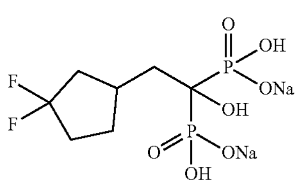 | ¹H-NMR (D₂O, 270 MHz) δ: 1.36-1.57 (1H, m), 1.66-2.27 (6H, m), 2.38-2.71 (2H, m).<br>MS m/z: 309 (M − 2Na + H)⁺. |
| Example 24 | 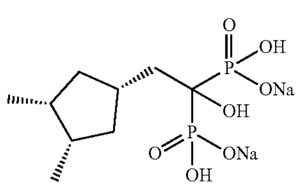 | ¹H-NMR (D₂O, 270 MHz) δ: 0.85 (6H, d, J = 6.5 Hz), 0.90-1.03 (2H, m), 1.86-2.34 (7H, m).<br>MS m/z: 301 (M − 2Na + H)⁺. |

TABLE 4

| Ex. | structure | Data |
|---|---|---|
| Example 25 | 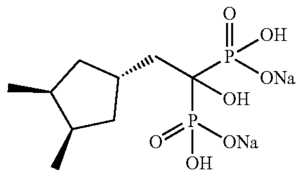 | ¹H-NMR (D₂O, 270 MHz) δ: 0.82 (6H, d, J = 6.8 Hz), 1.38-1.52 (2H, m), 1.58-1.70 (2H, m), 1.90-2.15 (4H, m), 2.55 (1H, sept, J = 7.6 Hz).<br>MS m/z: 301 (M − 2Na + H)⁺. |
| Example 26 | 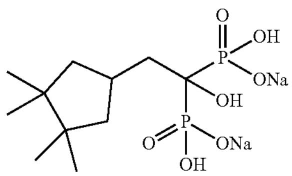 | ¹H-NMR (D₂O, 270 MHz) δ: 0.84 (6H, s), 1.40 (2H, dd, J = 13.0, 7.3 Hz), 1.88 (2H, dd, J = 13.0, 9.5 Hz), 2.07 (2H, dt, J = 5.4, 13.5 Hz), 2.46-2.60 (1H, m).<br>MS m/z: 329 (M − 2Na + H)⁺. |
| Example 27 | 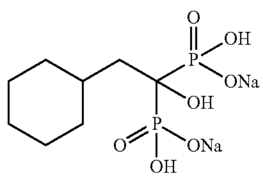 | ¹H-NMR (D₂O, 270 MHz) δ: 0.89-1.04 (2H, m), 1.07-1.19 (1H, m), 1.20-1.33 (2H, m), 1.54-1.67 (3H, m), 1.78-1.93 (5H, m),<br>³¹P-NMR (D₂O, 162 MHz) δ: 19.26<br>MS m/z: 287 (M − 2Na + H)⁺. |
| Example 28 | 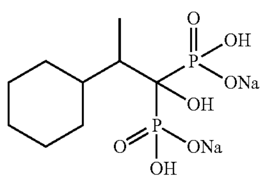 | ¹H-NMR (D₂O, 270 MHz) δ: 0.90-1.49 (9H, m), 1.50-1.73 (3H, m), 1.80-2.22 (3H, m).<br>MS m/z: 301 (M − 2Na + H)⁺. |
| Example 29 | 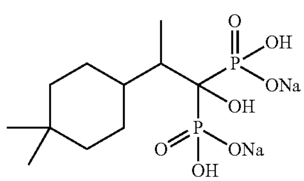 | ¹H-NMR (D₂O, 270 MHz) δ: 0.86 (6H, s), 1.14 (3H, d, J = 7.3 Hz), 1.19-1.60 (7H, m), 1.65-1.76 (1H, m), 1.94-2.25 (2H, m).<br>MS m/z: 329 (M − 2Na + H)⁺. |
| Example 30 | 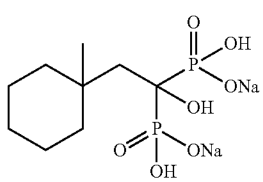 | ¹H-NMR (D₂O, 270 MHz) δ: 1.15 (3H, s), 1.19-1.56 (10H, m), 2.05 (2H, t, J = 14.0 Hz).<br>MS m/z: 301 (M − 2Na + H)⁺. |
| Example 31 | 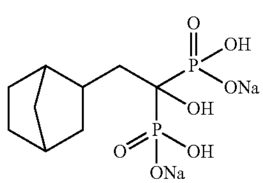 | ¹H-NMR (D₂O, 270 MHz) δ: 1.08-1.30 (4H, m), 1.32-1.66 (4H, m), 1.75-2.03 (2H, m), 2.04-2.25 (3H, m).<br>MS m/z: 299 (M − 2Na + H)⁺. |
| Example 32 | 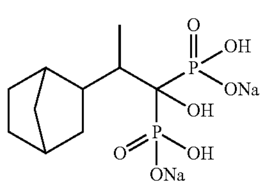 | ¹H-NMR (D₂O, 270 MHz) δ: 1.01-1.24 (6H, m), 1.26-1.50 (5H, m), 1.94-2.23 (3H, m), 2.34-2.48 (1H, m).<br>MS m/z: 313 (M − 2Na + H)⁺. |

TABLE 5

| Ex. | structure | Data |
|---|---|---|
| Example 33 | 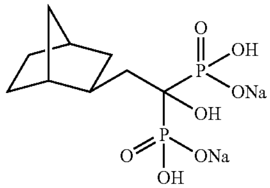 | ¹H-NMR (D₂O, 270 MHz) δ: 1.03-1.25 (4H, m), 1.26-1.64 (4H, m), 1.73-2.16 (3H, m), 2.15 (2H, s). <br> MS m/z: 299 (M − 2Na + H)⁺. |
| Example 34 | 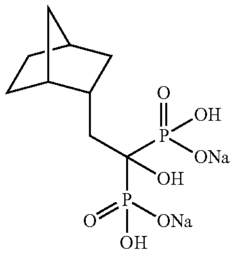 | ¹H-NMR (D₂O, 270 MHz) δ: 0.70-1.57 (7H, m), 1.84-2.25 (6H, m). <br> MS m/z: 299 (M − 2Na + H)⁺. |
| Example 35 | 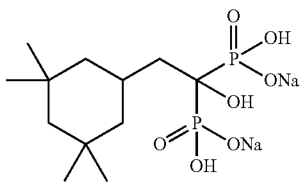 | ¹H-NMR (D₂O, 270 MHz) δ: 0.74 (1H, t, J = 12.4 Hz), 0.84 (6H, s), 0.99 (6H, s), 0.92-1.07 (1H, m), 1.14-1.31 (1H, m), 1.65 (2H, d, J = 13.0 Hz), 1.76-1.96 (2H, m), 2.18-2.37 (1H, m). <br> MS m/z: 343 (M − 2Na + H)⁺. |
| Example 36 | 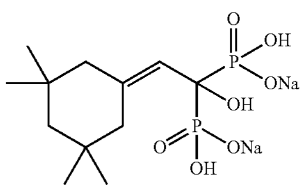 | ¹H-NMR (D₂O, 270 MHz) δ: 0.92 (6H, s), 0.95 (6H, s), 1.27 (2H, s), 1.90 (2H, br), 2.32 (2H, br), 5.56 (1H, t, J = 5.9 Hz). <br> MS m/z: 341 (M − 2Na + H)⁺. |
| Example 37 | 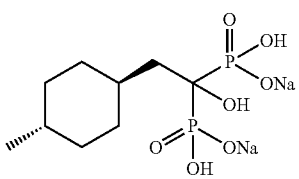 | ¹H-NMR (D₂O, 270 MHz) δ: 0.83 (3H, d, J = 6.5 Hz), 0.86-1.08 (4H, m), 1.14-1.36 (1H, m), 1.55-1.68 (2H, m), 1.72-1.95 (5H, m). <br> MS m/z: 301 (M − 2Na + H)⁺. |
| Example 38 | 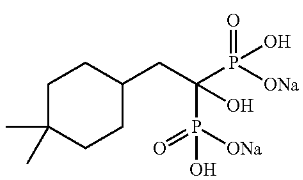 | ¹H-NMR (D₂O, 270 MHz) δ: 0.86 (6H, s), 1.12-1.37 (6H, m), 1.62-1.97 (5H, m). <br> MS m/z: 315 (M − 2Na + H)⁺. |
| Example 39 | 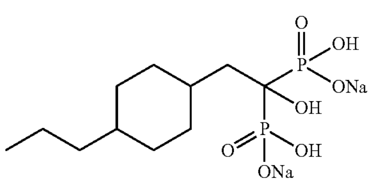 | ¹H-NMR (D₂O, 270 MHz) δ: 0.80-1.04 (6H, m), 1.10-1.60 (8H, m), 1.65-2.00 (5H, m). <br> MS m/z: 329 (M − 2Na + H)⁺. |
| Example 40 | 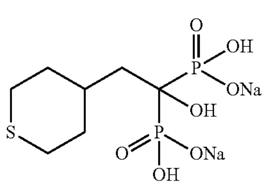 | ¹H-NMR (270 MHz) δ (D₂O): 1.35 (2H, ddd, J = 14.6, 10.8, 3.5 Hz), 1.82-2.06 (3H, m), 2.16-2.28 (2H, m), 2.52-2.78 (4H, m). <br> MS m/z: 305 (M − 2Na + H)⁺. |

TABLE 5-continued

| Ex. | structure | Data |
|---|---|---|
| Example 41 | (tetrahydrothiophen-3-ylmethyl bisphosphonate disodium structure) | ¹H-NMR (D₂O, 270 MHz) δ: 1.53-1.69 (1H, m), 1.99-2.24 (2H, m), 2.26-2.41 (1H, m), 2.51-2.71 (2H, m), 2.76-2.93 (2H, m), 3.12 (1H, dd, J = 9.7, 5.9 Hz). MS m/z: 291 (M − 2Na + H)⁺. |

TABLE 6

| Ex. | structure | Data |
|---|---|---|
| Example 42 | (1-(tetrahydrothiophen-3-yl)ethyl bisphosphonate disodium structure) | ¹H-NMR (D₂O, 270 MHz) δ: 1.16-1.24 (3H, m), 1.41-1.80 (1H, m), 2.24-2.68 (3H, m), 2.70-2.93 (3H, m), 3.04 (1H, dd, J = 6.5, 9.5 Hz). MS m/z: 305 (M − Na + H)⁺. |
| Example 43 | (tetrahydropyran-4-ylmethyl bisphosphonate disodium structure) | ¹H-NMR (D₂O, 270 MHz) δ: 1.25-1.45 (2H, m), 1.84-2.03 (4H, m), 2.10-2.30 (1H, m), 3.45-3.58 (2H, m), 3.88-4.00 (2H, m). MS m/z: 289 (M − 2Na + H)⁺. |
| Example 44 | (cycloheptylmethyl bisphosphonate disodium structure) | ¹H-NMR (D₂O, 270 MHz) δ: 1.20-1.67 (10H, m), 1.80-2.02 (4H, m), 2.03-2.17 (1H, m). MS m/z: 301 (M − 2Na + H)⁺. |
| Example 45 | (1-cycloheptylethyl bisphosphonate disodium structure) | ¹H-NMR (D₂O, 270 MHz) δ: 1.12 (3H, d, J = 7.0 Hz), 1.16-1.30 (1H, m), 1.36-1.70 (10H, m), 1.88-2.02 (1H, m), 2.08-2.26 (1H, m), 2.30-2.42 (1H, m). MS m/z: 315 (M − 2Na + H)⁺. |
| Example 46 | (cyclooctylmethyl bisphosphonate disodium structure) | ¹H-NMR (D₂O, 270 MHz) δ: 1.30-1.74 (12H, m), 1.75-2.05 (4H, m), 2.10-2.25 (1H, m). MS m/z: 315 (M − 2Na + H)⁺. |
| Example 47 | (cyclohexylmethyl bisphosphonate structure) | ¹H-NMR (D₂O, 400 MHz) δ: 0.87-1.02 (2H, m), 1.03-1.29 (3H, m), 1.50-1.66 (3H, m), 1.76-1.91 (5H, m). ³¹P-NMR (D₂O, 162 MHz) δ: 20.37. MS m/z: 287 (M − H)⁺. |

TABLE 6-continued

| Ex. | structure | Data |
|---|---|---|
| Example 48 | (structure) | $^1$H-NMR (D$_2$O, 400 MHz) δ: 0.91-1.04 (2H, m), 1.07-1.20 (1H, m), 1.21-1.34 (2H, m), 1.55-1.68 (3H, m), 1.79-1.95 (5H, m). $^{31}$P-NMR (D$_2$O, 162 MHz) δ: 19.39 MS m/z: 287 (M − 2Li + H)$^+$. |
| Example 49 | (structure) | $^1$H-NMR (D$_2$O, 400 MHz) δ: 0.87-1.01 (2H, m), 1.06-1.19 (1H, m), 1.20-1.33 (2H, m), 1.52-1.65 (3H, m), 1.75-1.95 (5H, m). $^{31}$P-NMR (D$_2$O, 162 MHz) δ: 19.61 MS m/z: 287 (M − 4Na + 3H)$^+$. |
| Example 50 | (structure) | $^1$H-NMR (D$_2$O, 400 MHz) δ: 0.89-1.03 (2H, m), 1.06-1.19 (1H, m), 1.20-1.33 (2H, m), 1.53-1.67 (3H, m), 1.78-1.93 (5H, m). $^{31}$P-NMR (D$_2$O, 162 MHz) δ: 19.37 MS m/z: 287 (M − 2K + H)$^+$. |

Test Example: Ectopic Calcification Inhibitory Effect in Vitamin D3-Induced Vascular Calcification Rat Model Male Wistar/ST rats were grouped according to their body weights as an index (6 individuals per group). Cholecalciferol (Wako Pure Chemical Industries, Ltd.) was subcutaneously administered at repeated doses of 125,000 IU/kg to each rat for 3 days to induce vascular calcification. Each test substance was orally administered at repeated doses once a day for 2 weeks from the day of administration of cholecalciferol. The rats were fasted from approximately 6 hours before the administration of the test substance to approximately 2 hours thereafter. On the day following the final administration, total blood was collected from the descending aorta of each rat under isoflurane anesthesia, and then, the aorta from the aortic root to the posterior limb bifurcation was excised. The aorta was chopped, then homogenized after adding 5 mL of 1 N hydrochloric acid and left at room temperature for 1 hour. After centrifugation at 15,000 rpm at 4° C. for 15 minutes, the obtained supernatant was used as a measurement sample. The amount of phosphorus in the measurement sample was measured using Phospha C-Test Wako (Wako Pure Chemical Industries, Ltd.) and used as an index for calcification. An average value of the amounts of aortic phosphorus in each group was determined to calculate the rate of inhibition of calcification by the administration of the test substance relative to a control (vehicle administration) (Table 7).

TABLE 7

Rate of inhibition of ectopic calcification by administration of test substance

| Example | Dose (mg/kg) | Rate of inhibition (%) |
|---|---|---|
| 3 | 10 | 64 |
| 4 | 5 | 39 |
| 6 | 30 | 95 |
| 7 | 5 | 51 |
| 8 | 3 | 22 |
| 11 | 5 | 57 |
| 12 | 5 | 28 |
| 13 | 5 | 53 |
| 14 | 5 | 29 |
| 15 | 5 | 87 |
| 16 | 5 | 75 |
| 17 | 5 | 80 |
| 18 | 5 | 53 |
| 20 | 5 | 46 |
| 21 | 5 | 68 |
| 23 | 5 | 43 |
| 24 | 5 | 93 |
| 25 | 5 | 64 |
| 26 | 5 | 66 |
| 27 | 5 | 82 |
| 28 | 30 | 95 |
| 30 | 5 | 47 |
| 31 | 3 | 29 |
| 35 | 5 | 71 |
| 44 | 10 | 95 |

Formulation Example 1 (Tablet)

Granules are produced using a fluidized bed such that one tablet comprises the compound of Example 1 (50 mg), lactose (73 mg), corn starch (15 mg), croscarmellose sodium (7.5 mg), hydroxypropylcellulose (3 mg) and magnesium stearate (1.5 mg). The granules and a lubricant are mixed and then compressed.

Formulation Example 2 (Injection Agent)

The compound of Example 1 (1 mg), D-mannitol (200 tag) and an appropriate amount of a pH adjuster are added, and the agent is produced by a freeze drying method.

INDUSTRIAL APPLICABILITY

The compound of the present invention shows an excellent ectopic calcification inhibitory effect and is particularly useful in the prevention and/or treatment of a disease associated with vascular calcification.

The invention claimed is:

1. A bisphosphonic acid compound of formula (1) or a pharmaceutically acceptable salt thereof:

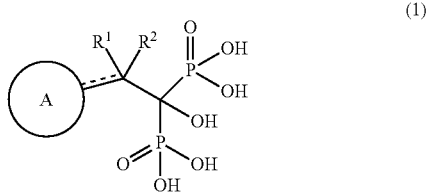

wherein - - - - - - represents a single bond or a double bond;

A represents a $C_{3-8}$ saturated cyclic hydrocarbon, wherein the saturated cyclic hydrocarbon is optionally substituted by 1 to 6 groups selected from the group consisting of a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group and a halogen atom; and $R^1$ and $R^2$ each independently represent a $C_{1-6}$ alkyl group, a $C_{2-6}$ alkenyl group, a $C_{2-6}$ alkynyl group, a $C_{1-6}$ alkoxy group, a $C_{6-10}$ aryloxy group, a $C_{1-6}$ haloalkoxy group, a $C_{1-6}$ haloalkyl group, a halogen atom or a hydrogen atom, wherein when - - - - - - is a double bond, $R^2$ is absent.

2. The bisphosphonic acid compound according to claim 1 or a pharmaceutically acceptable salt thereof, wherein - - - - - - is a single bond.

3. The bisphosphonic acid compound according to claim 1 or a pharmaceutically acceptable salt thereof, wherein A is a $C_{3-8}$ saturated cyclic hydrocarbon, wherein the saturated cyclic hydrocarbon is optionally substituted by 1 to 4 groups selected from the group consisting of a $C_{1-6}$ alkyl group, a $C_{1-6}$ alkoxy group, a $C_{6-10}$ aryloxy group and a halogen atom.

4. The bisphosphonic acid compound according to claim 1 or a pharmaceutically acceptable salt thereof, wherein $R^1$ and $R^2$ are each independently a $C_{1-6}$ alkyl group, a halogen atom or a hydrogen atom.

5. A pharmaceutical composition, comprising:
the bisphosphonic acid compound according to claim 1 or a salt thereof.

6. A prophylactic drug for a disease associated with ectopic calcification, the prophylactic drug comprising:
the bisphosphonic acid compound according to claim 1 or a salt thereof as an active ingredient.

7. A method for producing a prophylactic drug for a disease associated with ectopic calcification, the method comprising:
contacting the bisphosphonic acid compound according to claim 1 with a pharmaceutical additive.

8. The bisphosphonic acid compound according to claim 1 or a salt thereof,
wherein the bisphosphonic acid is suitable for preventing a disease associated with ectopic calcification.

9. A method for preventing a disease associated with ectopic calcification, the method comprising:
administering an effective amount of the bisphosphonic acid compound according to claim 1 or a salt thereof to a subject in need thereof.

10. The method of claim 7, wherein the pharmaceutical additive is a at least one selected from the group consisting of a base, an excipient, a lubricant, a coating agent, a sugar coating agent, a wetting agent, a binder, a disintegrant, a solvent, a solubilizer, a dissolving agent, a dissolution aid, a suspending agent, a dispersing agent, an emulsifier, a surfactant, a tonicity agent, a buffer, a pH adjuster, a soothing agent, an antiseptic, a preservative, a stabilizer, an antioxidant, a colorant and a sweetener.

11. A therapeutic drug for a disease associated with ectopic calcification, the therapeutic drug comprising:
the bisphosphonic acid compound according to claim 1 or a salt thereof as an active ingredient.

12. A method for producing a therapeutic drug for a disease associated with ectopic calcification, the method comprising:
contacting the bisphosphonic acid compound according to claim 1 with a pharmaceutical additive.

13. The bisphosphonic acid compound according to claim 1 or a salt thereof,
wherein the bisphosphonic acid is suitable for treating a disease associated with ectopic calcification.

14. A method for treating a disease associated with ectopic calcification, the method comprising:
administering an effective amount of the bisphosphonic acid compound according to claim 1 or a salt thereof to a patient in need thereof.

15. The method of claim 12, wherein the pharmaceutical additive is a at least one selected from the group consisting of a base, an excipient, a lubricant, a coating agent, a sugar coating agent, a wetting agent, a binder, a disintegrant, a solvent, a solubilizer, a dissolving agent, a dissolution aid, a suspending agent, a dispersing agent, an emulsifier, a surfactant, a tonicity agent, a buffer, a pH adjuster, a soothing agent, an antiseptic, a preservative, a stabilizer, an antioxidant, a colorant and a sweetener.

* * * * *